(12) United States Patent
Jung et al.

(10) Patent No.: US 6,773,895 B2
(45) Date of Patent: Aug. 10, 2004

(54) METHOD FOR IDENTIFYING SUBSTANCES WHICH POSITIVELY INFLUENCE INFLAMMATORY CONDITIONS OF CHRONIC INFLAMMATORY AIRWAY DISEASES

(75) Inventors: Birgit Jung, Schwabenheim (DE); Norbert Kraut, Eberhardzell (DE); Stefan Mueller, Mainz (DE); Barbara Kistler, Pfungstadt (DE); Peter Seither, Risseg Halde (DE); Karsten Quast, Schemmerberg (DE); Andreas Weith, Eberhardzell (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/944,807

(22) Filed: Aug. 31, 2001

(65) Prior Publication Data

US 2002/0119494 A1 Aug. 29, 2002

Related U.S. Application Data

(60) Provisional application No. 60/233,748, filed on Sep. 19, 2000.

(30) Foreign Application Priority Data

Sep. 1, 2000 (GB) .............................. 0021484

(51) Int. Cl.$^7$ ...................... G01N 33/53; G01N 33/566
(52) U.S. Cl. .................... 435/7.21; 435/4; 435/7.1; 435/7.2; 435/7.24; 436/501
(58) Field of Search .............. 435/4, 7.1, 7.2, 435/7.21, 7.24; 436/501

(56) References Cited

U.S. PATENT DOCUMENTS 5,639,593 A    6/1997  Kriegler et al.
5,811,520 A  *  9/1998  Hawkins et al.

FOREIGN PATENT DOCUMENTS

WO    WO 00 06729 A    2/2000
WO    WO 00 31261 A    6/2000

OTHER PUBLICATIONS

Christophe et al., 2002, Scand. J. Immunol. 56:470–476.*
Takano et al., 1997, J. Exp. Med. 185:1693–1704.*
Wells, 1990, Biochemistry 29:8509–8517.*
Ngo et al., 1994, The Protein Folding Problem and Tertiary Structure Prediction, Merz et al., eds., Birkhauser, Boston, pp. 492–495.*
Bork, 2000, Genome Research 10:398–400.*
Skolnick et al., 2000, Trends in Biotech. 18(1):34–39.*
Doerks et al., 1998, Trends in Genetics 14:248–250.*
Smith et al., 1997, Nature Biotechnology 15:1222–1223.*
Brenner, 1999, Trends in Genetics 15:132–133.*
Bork et al., 1996, Trends in Genetics 12:425–427.*
Veillette, A. et al "High Expression of Inhibitory Receptor SHPS–1 and its Association with Protein–tyrosine Phosphatase SHP–1 in Macrophages" J. Bio. Chem., 1998 273(35):22719–22728.
Danielle, R. P. et al "Demonstration of a Formyl Peptide Receptor on Lung Macrophages Correlation of Binding Properties with Chemo Taxis and Release of Super Oxide Anion" Am. Rev. Resp. Dis., 1982, 126:274–280.

* cited by examiner

*Primary Examiner*—Elizabeth Kemmerer
(74) *Attorney, Agent, or Firm*—Robert P. Raymond; Susan K. Pocchiari; Mary-Ellen M. Devlin

(57) ABSTRACT

The present invention relates to substances which modulate receptors involved in inflammatory processes and whose modulated functions positively influence inflammatory diseases.

5 Claims, No Drawings

SEQUENCE LISTING

<160> NUMBER OF SEQ ID NOS: 24

<210> SEQ ID NO 1
<211> LENGTH: 1910
<212> TYPE: DNA
<213> ORGANISM: Homo sapiens

<400> SEQUENCE: 1
gaaaaggagc ttagctgctg gtgctgctgg caagatggaa accaacttct ccactcctct    60
gaatgaatat gaagaagtgt cctatgagtc tgctggctac actgttctgc ggatcctccc   120

-continued

```
attggtggtg cttggggtca cctttgtcct cggggtcctg ggcaatgggc ttgtgatctg      180
ggtggctgga ttccggatga cacgcacagt caccaccatc tgttacctga acctggcccc      240
ggctgacttt tctttcacgg ccacattacc attcctcatt gtctccatgg ccatgggaga      300
aaaatggcct tttggctggt tcctgtgtaa gttaattcac atcgtggtgg acatcaacct      360
ctttggaagt gtcttcttga ttggtttcat tgcactggac cgctgcattt gtgtcctgca      420
tccagtctgg gcccagaacc accgcactgt gagtctggcc atgaaggtga tcgtcggacc      480
ttggattctt gctctagtcc ttaccttgcc agttttcctc ttttgactc cagtaactat       540 tccaaatggg gacacatact gtactttcaa ctttgcatcc tggggtggca cccctgagga      600
gaggctgaag gtggccatta ccatgctgac agccagaggg attatccggt ttgtcattgg      660
ctttagcttg ccgatgtcca ttgttgccat ctgctatggg ctcattgcag ccaagatcca      720
caaaaagggc atgattaaat ccagccgtcc cttacgggtc ctcactgctg tggtggcttc      780
tttcttcatc tgttggtttc cctttcaact ggttgccctt ctgggcaccg tctggctcaa      840
agagatgttg ttctatggca agtacaaaat cattgacatc ctggttaacc caacgagctc      900
cctggccttc tcaacagct gcctcaaccc catgctttac gtctttgtgg gccaagactt       960
ccgagagaga ctgatccact ccctgcccac cagtctggag agggccctgt ctgaggactc     1020
agccccaact aatgacacgg ctgccaattc tgcttcacct cctgcagaga ctgagttaca     1080
ggcaatgtga ggatgggtc agggatattt tgagttctgt tcatcctacc ctaatgccag      1140
ttccagcttc atctacccct gagtcatatt gaggcattca aggatgcaca gctcaagtat     1200
ttattcagga aaaatgcttt tgtgtccctg atttggggct aagaaataga cagtcaggct     1260
actaaaatat tagtgttatt ttttgttttt tgacttctgc ctatacctg gggtaagtgg      1320 agttgggaaa tacaagaaga gaaagaccgg tggggatttg taagacttag atgagatagt     1380
gcataataag gggaagactt taaagtataa agtaaaatgt ttgctgtagg tttttttatag    1440 ctattaaaaa aaatcagatt atggaagttt tcttctattt ttagtttgct aagagttttc     1500 tgtttcttt tcttacatca tgagtggact ttgcatttta tcaaatgcat tttctacatg      1560
tattaagatg gtcatattat tcttcttctt ttatgtaaat cattataaat aatgttcatt     1620
aagttctgaa tgttaaacta ctcttgaatt cctggaataa accacactta gtcctgatgt     1680
actttaaata tttatatctc acaggagttg gttagaattt ctgtgtttat gtttatatac     1740
tgttatttca ctttttctac tatccttgct aagttttcat agaaaataag gaacaaagag     1800
aaacttgtaa tggtctctga aaaggaattg agaagtaatt cctctgattc tgttttctgg     1860
tgttatatct ttattaaata ttcagaaaaa ttcaccagtg aaaaaaaaa                  1910
```

<210> SEQ ID NO 2
<211> LENGTH: 351
<212> TYPE: PRT
<213> ORGANISM: Homo sapiens

<400> SEQUENCE: 2

```
Met Glu Thr Asn Phe Ser Thr Pro Leu Asn Glu Tyr Glu Glu Val Ser
 1               5                  10                  15

Tyr Glu Ser Ala Gly Tyr Thr Val Leu Arg Ile Leu Pro Leu Val Val
             20                  25                  30

Leu Gly Val Thr Phe Val Leu Gly Val Leu Gly Asn Gly Leu Val Ile
         35                  40                  45

Trp Val Ala Gly Phe Arg Met Thr Arg Thr Val Thr Thr Ile Cys Tyr
     50                  55                  60
```

```
Leu Asn Leu Ala Leu Ala Asp Phe Ser Phe Thr Ala Thr Leu Pro Phe
 65                  70                  75                  80

Leu Ile Val Ser Met Ala Met Gly Glu Lys Trp Pro Phe Gly Trp Phe
             85                   90                  95

Leu Cys Lys Leu Ile His Ile Val Val Asp Ile Asn Leu Phe Gly Ser
            100                 105                 110

Val Phe Leu Ile Gly Phe Ile Ala Leu Asp Arg Cys Ile Cys Val Leu
        115                 120                 125

His Pro Val Trp Ala Gln Asn His Arg Thr Val Ser Leu Ala Met Lys
130                 135                 140

Val Ile Val Gly Pro Trp Ile Leu Ala Leu Val Leu Thr Leu Pro Val
145                 150                 155                 160

Phe Leu Phe Leu Thr Thr Val Thr Ile Pro Asn Gly Asp Thr Tyr Cys
                165                 170                 175

Thr Phe Asn Phe Ala Ser Trp Gly Gly Thr Pro Glu Glu Arg Leu Lys
            180                 185                 190

Val Ala Ile Thr Met Leu Thr Ala Arg Gly Ile Ile Arg Phe Val Ile
        195                 200                 205

Gly Phe Ser Leu Pro Met Ser Ile Val Ala Ile Cys Tyr Gly Leu Ile
210                 215                 220

Ala Ala Lys Ile His Lys Lys Gly Met Ile Lys Ser Ser Arg Pro Leu
225                 230                 235                 240

Arg Val Leu Thr Ala Val Val Ala Ser Phe Phe Ile Cys Trp Phe Pro
                245                 250                 255

Phe Gln Leu Val Ala Leu Leu Gly Thr Val Trp Leu Lys Glu Met Leu
            260                 265                 270

Phe Tyr Gly Lys Tyr Lys Ile Ile Asp Ile Leu Val Asn Pro Thr Ser
        275                 280                 285

Ser Leu Ala Phe Phe Asn Ser Cys Leu Asn Pro Met Leu Tyr Val Phe
290                 295                 300

Val Gly Gln Asp Phe Arg Glu Arg Leu Ile His Ser Leu Pro Thr Ser
305                 310                 315                 320

Leu Glu Arg Ala Leu Ser Glu Asp Ser Ala Pro Thr Asn Asp Thr Ala
                325                 330                 335

Ala Asn Ser Ala Ser Pro Pro Ala Glu Thr Glu Leu Gln Ala Met
            340                 345                 350

<210> SEQ ID NO 3
<211> LENGTH: 2433
<212> TYPE: DNA
<213> ORGANISM: Homo sapiens

<400> SEQUENCE: 3
cagccgcggc ccatggagcc cgccggcccg gccccggcc gcctcgggcc gctgctctgc      60
ctgctgctcg ccgcgtcctg cgcctggtca ggagtggcgg gtgaggagga gctgcaggtg    120
attcagcctg acaagtccgt atcagttgca gctggagagt cggccattct gcactgcact    180
gtgacctccc tgatccctgt ggggcccatc cagtggttca gaggagctgg accagcccgg    240
gaattaatct acaatcaaaa agaaggccac ttccccgggg taacaactgt ttcagagtcc    300
acaaagagag aaaacatgga cttttccatc agcatcagta catcaccccc agcagatgcc    360
ggcacctact actgtgtgaa gttccggaaa gggagccctg acacggagtt taagtctgga    420
gcaggcactg agctgtctgt gcgtgccaaa ccctctgccc ccgtggtatc gggccctgcg    480
```

```
gcgagggcca cacctcagca cacagtgagc ttcacctgcg agtcccacgg cttctcaccc      540
agagacatca ccctgaaatg gttcaaaaat gggaatgagc tctcagactt ccagaccaac      600
gtggaccccg taggagagag cgtgtcctac agcatccaca gcacagccaa ggtggtgctg      660
acccgcgagg acgttcactc tcaagtcatc tgcgaggtgg cccacgtcac cttgcagggg      720
gaccctcttc gtgggactgc caacttgtct gagaccatcc gagttccacc caccttggag      780
gttactcaac agcccgtgag ggcagagaac caggtgaatg tcacctgcca ggtgaggaag      840 ttctacccc agagactaca gctgacctgg ttggagaatg gaaacgtgtc ccggacagaa       900
acggcctcaa ccgttacaga gaacaaggat ggtacctaca actggatgag ctggctcctg      960
gtgaatgtat ctgcccacag ggatgatgtg aagctcacct gccaggtgga gcatgacggg     1020
cagccagcgg tcagcaaaag ccatgacctg aaggtctcag cccacccgaa ggagcagggc     1080
tcaaataccg ccgctgagaa cactggatct aatgaacgga acatctatat tgtggtgggt     1140
gtggtgtgca ccttgctggt ggccctactg atggcggccc tctacctcgt ccgaatcaga     1200
cagaagaaag cccagggctc cacttcttct acaaggttgc atgagcccga agaatgcc       1260 agagaaataa cacaggacac aaatgatatc acatatgcag acctgaacct gcccaagggg     1320
aagaagcctg ctccccaggc tgcggagccc aacaaccaca cggagtatgc cagcattcag     1380
accagcccgc agcccgcgtc ggaggacacc ctcacctatg ctgacctgga catggtccac     1440
ctcaaccgga cccccaagca gccggccccc aagcctgagc cgtccttctc agagtacgcc     1500
agcgtccagg tcccgaggaa gtgaatggga ccgtggtttg ctctagcacc catctctacg     1560
cgctttcttg tcccacaggg agccgccgtg atgagcacag ccaacccagt tcccggaggg     1620
ctggggcggt gcaggctctg ggacccaggg gccagggtgg ctcttctctc cccaccctc     1680 cttggctctc cagcacttcc tgggcagcca cggccccctc ccccaacatt gccacacacc     1740
tggaggctga cgttgccaaa ccagccaggg aaccaacctg ggaagtggcc agaactgcct     1800
ggggtccaag aactcttgtg cctccgtcca tcaccatgtg ggttttgaag accctcgact     1860
gcctccccga tgctccgaag cctgatcttc cagggtgggg aggagaaaat cccacctccc     1920
ctgacctcca ccacctccac caccaccacc accaccacca ccaccactac caccaccacc     1980 caactgggc tagagtgggg aagatttccc ctttagatca aactgcccct tccatggaaa      2040
agctggaaaa aaactctgga acccatatcc aggcttggtg aggttgctgc caacagtcct     2100 ggcctcccc atccctaggc aaagagccat gagtcctgga ggaggagagg accctccca      2160 aaggactgga agcaaaaccc tctgcttcct tgggtccctc caagactccc tggggcccaa     2220
ctgtgttgct ccaccggac ccatctctcc cttctagacc tgagcttgcc cctccagcta     2280
gcactaagca acatctcgct gtaagcgcct gtaaattact gtgaaatgtg aaacgtgcaa     2340
tcttgaaact gaggtgttag aaaacttgat ctgtggtgtt ttgttttgtt ttttttctta     2400
aaacaacagc aacgtgaaaa aaaaaaaaaa aaa                                  2433
```

<210> SEQ ID NO 4
<211> LENGTH: 503
<212> TYPE: PRT
<213> ORGANISM: Homo sapiens

<400> SEQUENCE: 4

Met Glu Pro Ala Gly Pro Ala Pro Gly Arg Leu Gly Pro Leu Leu Cys
1               5                   10                  15

Leu Leu Leu Ala Ala Ser Cys Ala Trp Ser Gly Val Ala Gly Glu Glu
            20                  25                  30

-continued

```
Glu Leu Gln Val Ile Gln Pro Asp Lys Ser Val Ser Val Ala Ala Gly
     35                  40                  45
Glu Ser Ala Ile Leu His Cys Thr Val Thr Ser Leu Ile Pro Val Gly
 50                  55                  60
Pro Ile Gln Trp Phe Arg Gly Ala Gly Pro Ala Arg Glu Leu Ile Tyr
 65                  70                  75                  80
Asn Gln Lys Glu Gly His Phe Pro Arg Val Thr Thr Val Ser Glu Ser
                 85                  90                  95
Thr Lys Arg Glu Asn Met Asp Phe Ser Ile Ser Ile Ser Asn Ile Thr
                100                 105                 110
Pro Ala Asp Ala Gly Thr Tyr Tyr Cys Val Lys Phe Arg Lys Gly Ser
             115                 120                 125
Pro Asp Thr Glu Phe Lys Ser Gly Ala Gly Thr Glu Leu Ser Val Arg
             130                 135                 140
Ala Lys Pro Ser Ala Pro Val Val Ser Gly Pro Ala Ala Arg Ala Thr
145                 150                 155                 160
Pro Gln His Thr Val Ser Phe Thr Cys Glu Ser His Gly Phe Ser Pro
                165                 170                 175
Arg Asp Ile Thr Leu Lys Trp Phe Lys Asn Gly Asn Glu Leu Ser Asp
                180                 185                 190
Phe Gln Thr Asn Val Asp Pro Val Gly Glu Ser Val Ser Tyr Ser Ile
            195                 200                 205
His Ser Thr Ala Lys Val Val Leu Thr Arg Glu Asp Val His Ser Gln
 210                 215                 220
Val Ile Cys Glu Val Ala His Val Thr Leu Gln Gly Asp Pro Leu Arg
225                 230                 235                 240
Gly Thr Ala Asn Leu Ser Glu Thr Ile Arg Val Pro Pro Thr Leu Glu
                245                 250                 255
Val Thr Gln Gln Pro Val Arg Ala Glu Asn Gln Val Asn Val Thr Cys
            260                 265                 270
Gln Val Arg Lys Phe Tyr Pro Gln Arg Leu Gln Leu Thr Trp Leu Glu
            275                 280                 285
Asn Gly Asn Val Ser Arg Thr Glu Thr Ala Ser Thr Val Thr Glu Asn
290                 295                 300
Lys Asp Gly Thr Tyr Asn Trp Met Ser Trp Leu Leu Val Asn Val Ser
305                 310                 315                 320
Ala His Arg Asp Asp Val Lys Leu Thr Cys Gln Val Glu His Asp Gly
                325                 330                 335
Gln Pro Ala Val Ser Lys Ser His Asp Leu Lys Val Ser Ala His Pro
            340                 345                 350
Lys Glu Gln Gly Ser Asn Thr Ala Ala Glu Asn Thr Gly Ser Asn Glu
            355                 360                 365
Arg Asn Ile Tyr Ile Val Val Gly Val Val Cys Thr Leu Leu Val Ala
            370                 375                 380
Leu Leu Met Ala Ala Leu Tyr Leu Val Arg Ile Arg Gln Lys Lys Ala
385                 390                 395                 400
Gln Gly Ser Thr Ser Ser Thr Arg Leu His Glu Pro Glu Lys Asn Ala
                405                 410                 415
Arg Glu Ile Thr Gln Asp Thr Asn Asp Ile Thr Tyr Ala Asp Leu Asn
                420                 425                 430
Leu Pro Lys Gly Lys Lys Pro Ala Pro Gln Ala Ala Glu Pro Asn Asn
            435                 440                 445
```

```
His Thr Glu Tyr Ala Ser Ile Gln Thr Ser Pro Gln Pro Ala Ser Glu
    450                 455                 460
Asp Thr Leu Thr Tyr Ala Asp Leu Asp Met Val His Leu Asn Arg Thr
465                 470                 475                 480
Pro Lys Gln Pro Ala Pro Lys Pro Glu Pro Ser Phe Ser Glu Tyr Ala
            485                 490                 495
Ser Val Gln Val Pro Arg Lys
            500
```

<210> SEQ ID NO 5
<211> LENGTH: 759
<212> TYPE: DNA
<213> ORGANISM: Homo sapiens

<400> SEQUENCE: 5

```
ctgtgctgta aaacaagag taacattttt atattaaagt taaataaagt tacaactttg      60
aagagagttt ctgcaagaca tgacacaaag ctgctagcag aaaatcaaaa cgctgattaa    120
aagaagcacg gtatgatgac caaacataaa aagtgtttta taattgttgg tgttttaata    180
acaactaata ttattactct gatagttaaa ctaactcgag attctcagag tttatgcccc    240
tatgattgga ttggtttcca aaacaaatgc tattatttct ctaaagaaga aggagattgg    300
aattcaagta aatacaactg ttccactcaa catgccgacc taactataat tgacaacata    360
gaagaaatga attttcttag gcggtataaa tgcagttctg atcactggat tggactgaag    420
atggcaaaaa atcgaacagg acaatgggta catggagcta catttaccaa atcgtttggc    480
atgagaggga gtgaaggatg tgcctacctc agcgatgatg gtgcagcaac agctagatgt    540
tacaccgaaa gaaatggatt tgcaggaaa agaatacact aagttaatgt ctaagataat    600
ggggaaaata gaaaataaca ttattaagtg taaaaccagc aaagtacttt tttaattaaa    660
caaagttcga gttttgtacc tgtctggtta attctgctta cgtgtcaggc tacacataaa    720
agccacttca aagattggca aaaaaaaaaa aaaaaaaa                            759
```

<210> SEQ ID NO 6
<211> LENGTH: 149
<212> TYPE: PRT
<213> ORGANISM: Homo sapiens

<400> SEQUENCE: 6

```
Met Met Thr Lys His Lys Lys Cys Phe Ile Ile Val Gly Val Leu Ile
  1               5                  10                  15
Thr Thr Asn Ile Ile Thr Leu Ile Val Lys Leu Thr Arg Asp Ser Gln
                20                  25                  30
Ser Leu Cys Pro Tyr Asp Trp Ile Gly Phe Gln Asn Lys Cys Tyr Tyr
            35                  40                  45
Phe Ser Lys Glu Glu Gly Asp Trp Asn Ser Ser Lys Tyr Asn Cys Ser
         50                  55                  60
Thr Gln His Ala Asp Leu Thr Ile Ile Asp Asn Ile Glu Glu Met Asn
 65                  70                  75                  80
Phe Leu Arg Arg Tyr Lys Cys Ser Ser Asp His Trp Ile Gly Leu Lys
                 85                  90                  95
Met Ala Lys Asn Arg Thr Gly Gln Trp Val His Gly Ala Thr Phe Thr
                100                 105                 110
Lys Ser Phe Gly Met Arg Gly Ser Glu Gly Cys Ala Tyr Leu Ser Asp
            115                 120                 125
Asp Gly Ala Ala Thr Ala Arg Cys Tyr Thr Glu Arg Lys Trp Ile Cys
```

```
            130              135              140
Arg Lys Arg Ile His
145

<210> SEQ ID NO 7
<211> LENGTH: 1086
<212> TYPE: DNA
<213> ORGANISM: Homo sapiens

<400> SEQUENCE: 7
ctaaaggtcc cctccccgga gcggagcgca cctagggtcc ctcttccgtc cccccagccc      60
agctacccgt tcagaccagc agcctcgggg ggcaccccc gccagcctgc ctccctcccg     120
ctcagccctg ccaggggttcc ccagccatga atctcttccg attcctggga gacctctccc    180
acctcctcgc catcatcttg ctactgctca aaatctggaa gtcccgctcg tgcgccggaa    240
tttcagggaa gagccaggtc ctgtttgctg tggtgttcac tgcccgatat ctggacctct    300
tcaccaacta catctcactc tacaacacgt gtatgaaggt ggtctacata gcctgctcct    360
tcaccacggt ctggttgatt tatagcaagt tcaaagctac ttacgatggg aaccatgaca    420
cgttcagagt ggagttcctg gtcgttccca cagccattct ggcgttcctg gtcaatcatg    480
acttcacccc tctggagatc ctctggacct tctccatcta cctggagtca gtggccatct    540
gccgcagct gttcatggtg agcaagaccg gcgaggcgga gaccatcacc agccactact    600
tgttgcgct aggcgtttac cgcacgctct atctcttcaa ctggatctgg cgctaccatt    660
tcgagggctt cttcgacctc atcgccattg tggcaggcct ggtccagaca gtcctctact    720
gcgatttctt ctacctctat atcaccaaag tcctaaaggg gaagaagttg agtttgccgg    780
catagccccg gtcctctcca tctctctcct cggcagcagc gggaggcaga ggaaggcggc    840
agaagatgaa gagctttccc atccaggggt gactttttta agaacccacc tcttgtgctc    900
cccatcccgc ctcctgccgg gtttcagggg gacagtggag gatccaggtc ttggggagct    960
caggacttgg gctgtttgta gttttttgcc ttttagacaa gaaaaaaaaa tctttccact   1020
ctttagtttt tgattctgat gactcgttttt ttcttctact ctgtggcccc aaattttata  1080
aagtga                                                              1086

<210> SEQ ID NO 8
<211> LENGTH: 212
<212> TYPE: PRT
<213> ORGANISM: Homo sapiens

<400> SEQUENCE: 8

Met Asn Leu Phe Arg Phe Leu Gly Asp Leu Ser His Leu Leu Ala Ile
  1               5                  10                  15

Ile Leu Leu Leu Leu Lys Ile Trp Lys Ser Arg Ser Cys Ala Gly Ile
                 20                  25                  30

Ser Gly Lys Ser Gln Val Leu Phe Ala Val Val Phe Thr Ala Arg Tyr
         35                  40                  45

Leu Asp Leu Phe Thr Asn Tyr Ile Ser Leu Tyr Asn Thr Cys Met Lys
     50                  55                  60

Val Val Tyr Ile Ala Cys Ser Phe Thr Thr Val Trp Leu Ile Tyr Ser
 65                  70                  75                  80

Lys Phe Lys Ala Thr Tyr Asp Gly Asn His Asp Thr Phe Arg Val Glu
                 85                  90                  95

Phe Leu Val Ile Pro Thr Ala Ile Leu Ala Phe Leu Val Asn His Asp
            100                 105                 110
```

```
Phe Thr Pro Leu Glu Ile Leu Trp Thr Phe Ser Ile Tyr Leu Glu Ser
        115                 120                 125

Val Ala Ile Leu Pro Gln Leu Phe Met Val Ser Lys Thr Gly Glu Ala
    130                 135                 140

Glu Thr Ile Thr Ser His Tyr Leu Phe Ala Leu Gly Val Tyr Arg Thr
145                 150                 155                 160

Leu Tyr Leu Phe Asn Trp Ile Trp Arg Tyr His Phe Glu Gly Phe Phe
                165                 170                 175

Asp Leu Ile Ala Ile Val Ala Gly Leu Val Gln Thr Val Leu Tyr Cys
            180                 185                 190

Asp Phe Phe Tyr Leu Tyr Ile Thr Lys Val Leu Lys Gly Lys Lys Leu
        195                 200                 205

Ser Leu Pro Ala
    210

<210> SEQ ID NO 9
<211> LENGTH: 3992
<212> TYPE: DNA
<213> ORGANISM: Homo sapiens

<400> SEQUENCE: 9
ggcttcagga agggcagaca gagtgtccaa aagcgtgaga gcacgaagtg aggagaaggt      60
ggagaagaga gaagaggaag aggaagagga agagaggaag cggagggaac tgcggccagg    120
ctaaaagggg aagaagagga tcagcccaag gaggaggaag aggaaaacaa gacaaacagc    180
cagtgcagag gagaggaacg tgtgtccagt gtcccgatcc ctgcggagct agtagctgag    240
agctctgtgc cctgggcacc ttgcagccct gcacctgcct gccacttccc caccgaggcc    300
atgggcccag gagttctgct gctcctgctg gtggccacag cttggcatgg tcagggaatc    360
ccagtgatag agcccagtgt ccccgagctg gtcgtgaagc caggagcaac ggtgaccttg    420
cgatgtgtgg gcaatggcag cgtggaatgg gatggccccg catcacctca ctggaccctg    480
tactctgatg gctccagcag catcctcagc accaacaacg ctaccttcca aaacacgggg    540
acctatcgct gcactgagcc tggagacccc ctggaggca gcgccgccat ccacctctat    600
gtcaaagacc ctgcccggcc ctggaacgtg ctagcacagg aggtggtcgt gttcgaggac    660
caggacgcac tactgccctg tctgctcaca gacccggtgc tggaagcagg cgtctcgctg    720
gtgcgtgtgc gtggccggcc cctcatgcgc acaccaact actccttctc gccctggcat    780
ggcttcacca tccacagggc caagttcatt cagagccagg actatcaatg cagtgccctg    840
atgggtggca ggaaggtgat gtccatcagc atccggctga aagtgcagaa agtcatccca    900 gggccccag ccttgacact ggtgcctgca gagctggtgc ggattcgagg ggaggctgcc    960
cagatcgtgt gctcagccag cagcgttgat gttaactttg atgtcttcct ccaacacaac   1020
aacactaagc tcgcaatccc tcaacaatct gactttcata taaccgtta ccaaaaagtc   1080 ctgacccta acctcgatca agtagatttc caacatgccg gcaactactc ctgcgtggcc   1140
agcaacgtgc aggcaagca ctccacctcc atgttcttcc gggtggtaga gagtgcctac   1200
ttgaacttga gctctgagca gaacctcatc aggaggtga ccgtggggga ggggctcaac   1260
ctcaaagtca tggtggaggc ctacccaggc tgcaaggtt taactggac ctacctggga   1320 cccttttctg accaccagcc tgagcccaag cttgctaatg ctaccaccaa ggacacatac   1380
aggcacacct tcaccctctc tctgcccgc ctgaagccct tgaggctgg ccgctactcc    1440 ttcctggcca gaaacccagg aggctggaga gctctgacgt ttgagctcac ccttcgatac   1500
```

```
cccccagagg taagcgtcat atggacattc atcaacggct ctggcaccct tttgtgtgct   1560
gcctctgggt accccagcc caacgtgaca tggctgcagt gcagtggcca cactgatagg   1620
tgtgatgagg cccaagtgct gcaggtctgg gatgacccat accctgaggt cctgagccag   1680
gagcccttcc acaaggtgac ggtgcagagc ctgctgactg ttgagacctt agagcacaac   1740
caaacctacg agtgcagggc ccacaacagc gtggggagtg ctcctgggc cttcataccc   1800 atctctgcag gagcccacac gcatccccg gatgagttcc tcttcacacc agtggtggtc   1860
gcctgcatgt ccatcatggc cttgctgctg ctgctgctcc tgctgctatt gtacaagtat   1920
aagcagaagc ccaagtacca ggtccgctgg aagatcatcg agagctatga gggcaacagt   1980
tatactttca tcgaccccac gcagctgcct tacaacgaga agtgggagtt cccccggaac   2040
aacctgcagt ttggtaagac cctcggagct ggagcctttg ggaaggtggt ggaggccacg   2100
gcctttggtc tgggcaagga ggatgctgtc ctgaaggtgg ctgtgaagat gctgaagtcc   2160
acggcccatg ctgatgagaa ggaggccctc atgtccgagc tgaagatcat gagccacctg   2220
ggccagcacg agaacatcgt caaccttctg ggagcctgta cccatggagg ccctgtactg   2280
gtcatcacgg agtactgttg ctatggcgac ctgctcaact ttctgcgaag gaaggctgag   2340
gccatgctgg acccagcct gagccccggc caggaccccg agggaggcgt cgactataag   2400
aacatccacc tcgagaagaa atatgtccgc agggacagtg gcttctccag ccagggtgtg   2460
gacacctatg tggagatgag gcctgtctcc acttcttcaa atgactcctt ctctgagcaa   2520
gacctggaca aggaggatgg acggcccctg gagctccggg acctgcttca cttctccagc   2580
caagtagccc agggcatggc cttcctcgct tccaagaatt gcatccaccg ggacgtggca   2640
gcgcgtaacg tgctgttgac caatggtcat gtggccaaga ttggggactt cgggctggct   2700
agggacatca tgaatgactc caactacatt gtcaagggca atgcccgcct gcctgtgaag   2760
tggatggccc cagagagcat cttttgactgt gtctacacgg ttcagagcga cgtctggtcc   2820
tatggcatcc tcctctggga gatcttctca cttgggctga atccctaccc tggcatcctg   2880
gtgaacagca agttctataa actggtgaag gatggatacc aaatggccca gcctgcattt   2940
gccccaaaga atatatacag catcatgcag gcctgctggg ccttggagcc cacccacaga   3000
cccaccttcc agcagatctg ctccttcctt caggagcagg cccaagagga caggagagag   3060
cgggactata ccaatctgcc gagcagcagc agaagcggtg gcagcggcag cagcagcagt   3120
gagctggagg aggagagctc tagtgagcac ctgacctgct gcgagcaagg ggatatcgcc   3180
cagcccttgc tgcagcccaa caactatcag ttctgctgag gagttgacga cagggagtac   3240
cactctcccc tcctccaaac ttcaactcct ccatggatgg ggcgacacgg ggagaacata   3300
caaactctgc cttcggtcat ttcactcaac agctcggccc agtctgaaa cttgggaagg   3360 tgagggattc aggggaggtc agaggatccc acttcctgag catgggccat cactgccagt   3420
caggggctgg gggctgagcc ctcacccccc gcctccccta ctgttctcat ggtgttggcc   3480
tcgtgtttgc tatgccaact agtagaacct tctttcctaa tcccttatc ttcatggaaa   3540 tggactgact ttatgcctat gaagtcccca ggagctacac tgatactgag aaaaccaggc   3600 tctttgggc tagacagact ggcagagagt gagatctccc tctctgagag gagcagcaga   3660
tgctcacaga ccacactcag ctcaggcccc ttggagcagg atggctcctc taagaatctc   3720
acaggacctc ttagtctctg ccctatacgc cgccttcact ccacagcctc acccctccca   3780 ccccatact ggtactgctg taatgagcca agtggcagct aaaagttggg ggtgttctgc   3840
```

```
ccagtcccgt cattctgggc tagaaggcag gggaccttgg cattggctgg ccacaccaag      3900
caggaagcac aaactccccc aagctgactc atcctaacta acagtcacgc cgtgggatgt      3960
ctctgtccac attaaactaa cagcattaat gc                                    3992
```

<210> SEQ ID NO 10
<211> LENGTH: 972
<212> TYPE: PRT
<213> ORGANISM: Homo sapiens

<400> SEQUENCE: 10

```
Met Gly Pro Gly Val Leu Leu Leu Leu Val Ala Thr Ala Trp His
 1               5                  10                  15

Gly Gln Gly Ile Pro Val Ile Glu Pro Ser Val Pro Glu Leu Val Val
                20                  25                  30

Lys Pro Gly Ala Thr Val Thr Leu Arg Cys Val Gly Asn Gly Ser Val
            35                  40                  45

Glu Trp Asp Gly Pro Pro Ser Pro His Trp Thr Leu Tyr Ser Asp Gly
    50                  55                  60

Ser Ser Ile Leu Ser Thr Asn Asn Ala Thr Phe Gln Asn Thr Gly
65                  70                  75                  80

Thr Tyr Arg Cys Thr Glu Pro Gly Asp Pro Leu Gly Gly Ser Ala Ala
                85                  90                  95

Ile His Leu Tyr Val Lys Asp Pro Ala Arg Pro Trp Asn Val Leu Ala
            100                 105                 110

Gln Glu Val Val Phe Glu Asp Gln Asp Ala Leu Leu Pro Cys Leu
        115                 120                 125

Leu Thr Asp Pro Val Leu Glu Ala Gly Val Ser Leu Val Arg Val Arg
    130                 135                 140

Gly Arg Pro Leu Met Arg His Thr Asn Tyr Ser Phe Ser Pro Trp His
145                 150                 155                 160

Gly Phe Thr Ile His Arg Ala Lys Phe Ile Gln Ser Gln Asp Tyr Gln
                165                 170                 175

Cys Ser Ala Leu Met Gly Gly Arg Lys Val Met Ser Ile Ser Ile Arg
            180                 185                 190

Leu Lys Val Gln Lys Val Ile Pro Gly Pro Pro Ala Leu Thr Leu Val
        195                 200                 205

Pro Ala Glu Leu Val Arg Ile Arg Gly Glu Ala Ala Gln Ile Val Cys
    210                 215                 220

Ser Ala Ser Ser Val Asp Val Asn Phe Asp Val Phe Leu Gln His Asn
225                 230                 235                 240

Asn Thr Lys Leu Ala Ile Pro Gln Gln Ser Asp Phe His Asn Asn Arg
                245                 250                 255

Tyr Gln Lys Val Leu Thr Leu Asn Leu Asp Gln Val Asp Phe Gln His
            260                 265                 270

Ala Gly Asn Tyr Ser Cys Val Ala Ser Asn Val Gln Gly Lys His Ser
        275                 280                 285

Thr Ser Met Phe Phe Arg Val Val Glu Ser Ala Tyr Leu Asn Leu Ser
    290                 295                 300

Ser Glu Gln Asn Leu Ile Gln Glu Val Thr Val Gly Glu Gly Leu Asn
305                 310                 315                 320

Leu Lys Val Met Val Glu Ala Tyr Pro Gly Leu Gln Gly Phe Asn Trp
                325                 330                 335

Thr Tyr Leu Gly Pro Phe Ser Asp His Gln Pro Glu Pro Lys Leu Ala
            340                 345                 350
```

```
Asn Ala Thr Thr Lys Asp Thr Tyr Arg His Thr Phe Thr Leu Ser Leu
        355                 360                 365

Pro Arg Leu Lys Pro Ser Glu Ala Gly Arg Tyr Ser Phe Leu Ala Arg
        370                 375                 380

Asn Pro Gly Gly Trp Arg Ala Leu Thr Phe Glu Leu Thr Leu Arg Tyr
385                 390                 395                 400

Pro Pro Glu Val Ser Val Ile Trp Thr Phe Ile Asn Gly Ser Gly Thr
                    405                 410                 415

Leu Leu Cys Ala Ala Ser Gly Tyr Pro Gln Pro Asn Val Thr Trp Leu
            420                 425                 430

Gln Cys Ser Gly His Thr Asp Arg Cys Asp Glu Ala Gln Val Leu Gln
            435                 440                 445

Val Trp Asp Asp Pro Tyr Pro Glu Val Leu Ser Gln Glu Pro Phe His
        450                 455                 460

Lys Val Thr Val Gln Ser Leu Leu Thr Val Glu Thr Leu Glu His Asn
465                 470                 475                 480

Gln Thr Tyr Glu Cys Arg Ala His Asn Ser Val Gly Ser Gly Ser Trp
                    485                 490                 495

Ala Phe Ile Pro Ile Ser Ala Gly Ala His Thr His Pro Pro Asp Glu
            500                 505                 510

Phe Leu Phe Thr Pro Val Val Ala Cys Met Ser Ile Met Ala Leu
        515                 520                 525

Leu Leu Leu Leu Leu Leu Leu Leu Leu Tyr Lys Tyr Lys Gln Lys Pro
        530                 535                 540

Lys Tyr Gln Val Arg Trp Lys Ile Ile Glu Ser Tyr Glu Gly Asn Ser
545                 550                 555                 560

Tyr Thr Phe Ile Asp Pro Thr Gln Leu Pro Tyr Asn Glu Lys Trp Glu
                    565                 570                 575

Phe Pro Arg Asn Asn Leu Gln Phe Gly Lys Thr Leu Gly Ala Gly Ala
            580                 585                 590

Phe Gly Lys Val Val Glu Ala Thr Ala Phe Gly Leu Gly Lys Glu Asp
        595                 600                 605

Ala Val Leu Lys Val Ala Val Lys Met Leu Lys Ser Thr Ala His Ala
        610                 615                 620

Asp Glu Lys Glu Ala Leu Met Ser Glu Leu Lys Ile Met Ser His Leu
625                 630                 635                 640

Gly Gln His Glu Asn Ile Val Asn Leu Leu Gly Ala Cys Thr His Gly
                    645                 650                 655

Gly Pro Val Leu Val Ile Thr Glu Tyr Cys Cys Tyr Gly Asp Leu Leu
            660                 665                 670

Asn Phe Leu Arg Arg Lys Ala Glu Ala Met Leu Gly Pro Ser Leu Ser
        675                 680                 685

Pro Gly Gln Asp Pro Glu Gly Gly Val Asp Tyr Lys Asn Ile His Leu
        690                 695                 700

Glu Lys Lys Tyr Val Arg Arg Asp Ser Gly Phe Ser Ser Gln Gly Val
705                 710                 715                 720

Asp Thr Tyr Val Glu Met Arg Pro Val Ser Thr Ser Ser Asn Asp Ser
                    725                 730                 735

Phe Ser Glu Gln Asp Leu Asp Lys Glu Asp Gly Arg Pro Leu Glu Leu
            740                 745                 750

Arg Asp Leu Leu His Phe Ser Ser Gln Val Ala Gln Gly Met Ala Phe
        755                 760                 765
```

-continued

```
Leu Ala Ser Lys Asn Cys Ile His Arg Asp Val Ala Ala Arg Asn Val
    770                 775                 780
Leu Leu Thr Asn Gly His Val Ala Lys Ile Gly Asp Phe Gly Leu Ala
785                 790                 795                 800
Arg Asp Ile Met Asn Asp Ser Asn Tyr Ile Val Lys Gly Asn Ala Arg
                805                 810                 815
Leu Pro Val Lys Trp Met Ala Pro Glu Ser Ile Phe Asp Cys Val Tyr
            820                 825                 830
Thr Val Gln Ser Asp Val Trp Ser Tyr Gly Ile Leu Leu Trp Glu Ile
        835                 840                 845
Phe Ser Leu Gly Leu Asn Pro Tyr Pro Gly Ile Leu Val Asn Ser Lys
850                 855                 860
Phe Tyr Lys Leu Val Lys Asp Gly Tyr Gln Met Ala Gln Pro Ala Phe
865                 870                 875                 880
Ala Pro Lys Asn Ile Tyr Ser Ile Met Gln Ala Cys Trp Ala Leu Glu
                885                 890                 895
Pro Thr His Arg Pro Thr Phe Gln Gln Ile Cys Ser Phe Leu Gln Glu
            900                 905                 910
Gln Ala Gln Glu Asp Arg Arg Glu Arg Asp Tyr Thr Asn Leu Pro Ser
        915                 920                 925
Ser Ser Arg Ser Gly Gly Ser Gly Ser Ser Ser Glu Leu Glu Glu
930                 935                 940
Glu Ser Ser Ser Glu His Leu Thr Cys Cys Glu Gln Gly Asp Ile Ala
945                 950                 955                 960
Gln Pro Leu Leu Gln Pro Asn Asn Tyr Gln Phe Cys
                965                 970

<210> SEQ ID NO 11
<211> LENGTH: 1696
<212> TYPE: DNA
<213> ORGANISM: Homo sapiens

<400> SEQUENCE: 11
ccgagtgtcc acaccctgtg cgtctctctg tcctgccagc actgagggct catccatccg    60
cagagcaggg cagtgggagg agacgccatg accccccatcc tcacggtcct gatctgtctc   120
gggctgagtc tggccccag gacccacgtg caggcagggc acctcccaa gcccacctc      180
tgggctgagc caggctctgt gatcatccag ggaagtcctg tgaccctcag gtgtcagggg   240
agccttcagg ctgaggagta ccatctatat agggaaaaca aatcagcatc ctgggttaga   300
cggatacaag agcctgggaa gaatggccag ttccccatcc catccatcac ctgggaacac   360
gcagggcggt atcactgtca gtactacagc cacaatcact catcagagta cagtgacccc   420
ctggagctgg tggtgacagg agcctacagc aaacccaccc tctcagctct gcccagccct   480
gtggtgacct taggagggaa cgtgaccctc agtgtgtct cacaggtggc atttgacggc   540
ttcattctgt gtaaggaagg agaagatgaa cacccacaac gcctgaactc ccattcccat   600
gcccgtgggg ggtcctgggc catcttctcc gtgggcccg tgagcccgag tcgcaggtgg   660
tcgtacaggt gctatgctta tgactcgaac tctccctatg tgtggtctct acccagtgat   720
ctcctggagc tcctggtccc aggtgttttct aagaagccat cactctcagt gcagccaggt   780
cctatggtgg ccctgggga gagcctgacc ctccagtgtg tctctgatgt cggctacgac   840
agatttgttc tgtataagga gggagaacgt gacttcctcc agcgcctgg ttggcagccc   900
caggctgggc tctcccaggc caacttcacc ctgggccctg tgagccctc ccacgggggc   960
```

-continued

```
cagtacagat gctacagtgc acacaacctc tcctccgagt ggtcggcccc cagtgacccc    1020
ctggacatcc tgatcacagg acagttctat gacagaccct ctctctcggt gcagccggtc    1080
cccacagtag ccccaggaaa gaacgtgacc ctgctgtgtc agtcacgggg gcagttccac    1140
actttccttc tgaccaagga gggggcaggc catcccccac tgcatctgag atcagagcac    1200
caagctcagc agaaccaggc tgaattccgc atgggtcctg tgacctcagc ccacgtgggg    1260
acctacagat gctacagctc actcagctcc aaccctacc tgctgtctct ccccagtgac    1320
cccctggagc tcgtggtctc agcatccta ggccaacacc cccaggatta cacagtggag    1380
aatctcatcc gcatgggtgt ggctggcttg gtcctggtgg tcctcgggat tctgctattt    1440
gaggctcagc acagccagag aagcctacaa gatgcagccg ggaggtgaac agcagagagg    1500
acaatgcata cttcagcgtg gtggagcctc aggacagat ctgatgatcc caggaggctc    1560
tggaggacaa tctaggacct acattatctg gactgtatgc tggtcatttc tagagacagc    1620
aatcaatatt tgagtgtaag gaaactgtct ggggtgattc ctagaagatc attaaactgt    1680
ggtacatttt tttgtc                                                    1696
```

<210> SEQ ID NO 12
<211> LENGTH: 466
<212> TYPE: PRT
<213> ORGANISM: Homo sapiens

<400> SEQUENCE: 12

```
Met Thr Pro Ile Leu Thr Val Leu Ile Cys Leu Gly Leu Ser Leu Gly
  1               5                  10                  15

Pro Arg Thr His Val Gln Ala Gly His Leu Pro Lys Pro Thr Leu Trp
             20                  25                  30

Ala Glu Pro Gly Ser Val Ile Ile Gln Gly Ser Pro Val Thr Leu Arg
         35                  40                  45

Cys Gln Gly Ser Leu Gln Ala Glu Glu Tyr His Leu Tyr Arg Glu Asn
     50                  55                  60

Lys Ser Ala Ser Trp Val Arg Arg Ile Gln Glu Pro Gly Lys Asn Gly
 65                  70                  75                  80

Gln Phe Pro Ile Pro Ser Ile Thr Trp Glu His Ala Gly Arg Tyr His
                 85                  90                  95

Cys Gln Tyr Tyr Ser His Asn His Ser Ser Glu Tyr Ser Asp Pro Leu
            100                 105                 110

Glu Leu Val Val Thr Gly Ala Tyr Ser Lys Pro Thr Leu Ser Ala Leu
        115                 120                 125

Pro Ser Pro Val Val Thr Leu Gly Gly Asn Val Thr Leu Gln Cys Val
    130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
                165                 170                 175

Trp Ala Ile Phe Ser Val Gly Pro Val Ser Pro Ser Arg Arg Trp Ser
            180                 185                 190

Tyr Arg Cys Tyr Ala Tyr Asp Ser Asn Ser Pro Tyr Val Trp Ser Leu
        195                 200                 205

Pro Ser Asp Leu Leu Glu Leu Leu Val Pro Gly Val Ser Lys Lys Pro
    210                 215                 220

Ser Leu Ser Val Gln Pro Gly Pro Met Val Ala Pro Gly Glu Ser Leu
225                 230                 235                 240
```

```
Thr Leu Gln Cys Val Ser Asp Val Gly Tyr Asp Arg Phe Val Leu Tyr
            245                 250                 255
Lys Glu Gly Glu Arg Asp Phe Leu Gln Arg Pro Gly Trp Gln Pro Gln
        260                 265                 270
Ala Gly Leu Ser Gln Ala Asn Phe Thr Leu Gly Pro Val Ser Pro Ser
    275                 280                 285
His Gly Gly Gln Tyr Arg Cys Tyr Ser Ala His Asn Leu Ser Ser Glu
290                 295                 300
Trp Ser Ala Pro Ser Asp Pro Leu Asp Ile Leu Ile Thr Gly Gln Phe
305                 310                 315                 320
Tyr Asp Arg Pro Ser Leu Ser Val Gln Pro Val Pro Thr Val Ala Pro
                325                 330                 335
Gly Lys Asn Val Thr Leu Leu Cys Gln Ser Arg Gly Gln Phe His Thr
            340                 345                 350
Phe Leu Leu Thr Lys Glu Gly Ala Gly His Pro Pro Leu His Leu Arg
        355                 360                 365
Ser Glu His Gln Ala Gln Gln Asn Gln Ala Glu Phe Arg Met Gly Pro
    370                 375                 380
Val Thr Ser Ala His Val Gly Thr Tyr Arg Cys Tyr Ser Ser Leu Ser
385                 390                 395                 400
Ser Asn Pro Tyr Leu Leu Ser Leu Pro Ser Asp Pro Leu Glu Leu Val
                405                 410                 415
Val Ser Ala Ser Leu Gly Gln His Pro Gln Asp Tyr Thr Val Glu Asn
            420                 425                 430
Leu Ile Arg Met Gly Val Ala Gly Leu Val Leu Val Val Leu Gly Ile
        435                 440                 445
Leu Leu Phe Glu Ala Gln His Ser Gln Arg Ser Leu Gln Asp Ala Ala
    450                 455                 460
Gly Arg
465

<210> SEQ ID NO 13
<211> LENGTH: 63
<212> TYPE: DNA
<213> ORGANISM: Artificial Sequence
<220> FEATURE:
<223> OTHER INFORMATION: Description of Artificial Sequence: Primer

<400> SEQUENCE: 13
ggccagtgaa ttgtaatacg actcactata gggaggcggt tttttttttt tttttttttt     60
ttt                                                                  63

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 14
gtcgtcaaga tgctaccgtt cagga                                           25

<210> SEQ ID NO 15
<211> LENGTH: 48
<212> TYPE: DNA
<213> ORGANISM: Artificial Sequence
<220> FEATURE:
<223> OTHER INFORMATION: Description of Artificial Sequence: Primer
```

-continued

<400> SEQUENCE: 15
ggggacaagt tgtacaaaa agcaggcta tggaaaccaa cttctcca          48

<210> SEQ ID NO 16
<211> LENGTH: 53
<212> TYPE: DNA
<213> ORGANISM: Artificial Sequence
<220> FEATURE:
<223> OTHER INFORMATION: Description of Artificial Sequence: Primer

<400> SEQUENCE: 16
ggggaccact tgtacaaga aagctgggtt cacattgcct gtaactcagt ctc    53

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
agcccatagc agatggcaac                                        20

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 18
tgtactttca actttgcatc ctgg                                   24

<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 19
aagccaatga caaaccggat aatccctc                               28

<210> SEQ ID NO 20
<211> LENGTH: 2051
<212> TYPE: DNA
<213> ORGANISM: Homo sapiens

<400> SEQUENCE: 20
cgccactttg ctggagcatt cactaggcga ggcgctccat cggactcact agccgcactc    60
atgaatcggc accatctgca ggatcacttt ctggaaatag acaagaagaa ctgctgtgtg   120
ttccgagatg acttcattgc caaggtgttg ccgccggtgt ggggctgga gtttatcttt   180 gggcttctgg gcaatggcct tgccctgtgg attttctgtt tccacctcaa gtcctggaaa   240
tccagccgga ttttcctgtt caacctggca gtagctgact ttctactgat catctgcctg   300
ccgttcgtga tggactacta tgtgcggcgt tcagactgga ctttgggga catcccttgc   360 cggctggtgc tcttcatgtt tgccatgaac cgcagggca gcatcatctt cctcacggtg   420
gtggcggtag acaggtattt ccgggtggtc catccccacc acgccctgaa caagatctcc   480
aattggacag cagccatcat ctcttgcctt ctgtggggca tcactgttgg cctaacagtc   540
cacctcctga gaagaagtt gctgatccag aatggccctg caaatgtgtg catcagcttc   600

```
agcatctgcc ataccttccg gtggcacgaa gctatgttcc tcctggagtt cctcctgccc    660
ctgggcatca tcctgttctg ctcagccaga attatctgga gcctgcggca gagacaaatg    720
gaccggcatg ccaagatcaa gagagccatc accttcatca tggtggtggc catcgtcttt    780
gtcatctgct ccttcccag cgtggttgtg cggatccgca tcttctggct cctgcacact    840
tcgggcacgc agaattgtga agtgtaccgc tcggtggacc tggcgttctt tatcactctc    900
agcttcacct acatgaacag catgctggac cccgtggtgt actacttctc cagcccatcc    960
tttcccaact tcttctccac tttgatcaac cgctgcctcc agaggaagat gacaggtgag   1020
ccagataata accgcagcac gagcgtcgag ctcacagggg accccaacaa accagaggc    1080 gctccagagg cgttaatggc caactccggt gagccatgga gccctcta tctgggccca    1140 acctcaaata accattccaa gaagggacat tgtcaccaag aaccagcatc tctggagaaa   1200
cagttgggct gttgcatcga gtaatgtcac tggactcggc taaggtttc ctggaacttc    1260 cagattcaga gaatctgatt tagggaaact gtggcagatg agtgggagac tggttgcaag   1320
gtgtgaccac aggaatcctg gaggaacaga gagtaaagct tctaggcatc tgaaacttgc   1380
ttcatctctg acgctcgcag gactgaagat gggcaaattg taggcgtttc tgctgagcag   1440
agttggagcc agagatctac ttgtgacttg ttggccttct tcccacatct gcctcagact   1500 gggggggct cagctcctcg ggtgatatct agcctgcttg tgagctctag cagggataag   1560
gagagctgag attggaggga attgtgttgc tcctggagga agcccaggca tcattaaaca   1620
agccagtagg tcacctggct tccgtggacc aattcatctt tcagacaagc tttagagaaa   1680
tggactcagg gaagagactc acatgctttg gttagtatct gtgtttccgg tgggtgtaat   1740 agggattag ccccagaagg gactgagcta acagtgtta ttatgggaaa ggaaatggca    1800
ttgctgcttt caaccagcga ctaatgcaat ccattcctct cttgtttata gtaatctaag   1860
ggttgagcag ttaaaacggc ttcaggatag aaagctgttt cccacctgtt tcgttttacc   1920
attaaaaggg aaacgtgcct ctgccccacg ggtagagggg gtgcacgttc ctcctggttc   1980
cttcgcttgt gtttctgtac ttaccaaaaa tctaccactt caataaattt tgataggaga   2040 caaaaaaaa a                                                          2051
```

<210> SEQ ID NO 21
<211> LENGTH: 387
<212> TYPE: PRT
<213> ORGANISM: Homo sapiens

<400> SEQUENCE: 21

```
Met Asn Arg His His Leu Gln Asp His Phe Leu Glu Ile Asp Lys Lys
  1               5                  10                  15

Asn Cys Cys Val Phe Arg Asp Asp Phe Ile Ala Lys Val Leu Pro Pro
                 20                  25                  30

Val Leu Gly Leu Glu Phe Ile Phe Gly Leu Leu Gly Asn Gly Leu Ala
             35                  40                  45

Leu Trp Ile Phe Cys Phe His Leu Lys Ser Trp Lys Ser Ser Arg Ile
         50                  55                  60

Phe Leu Phe Asn Leu Ala Val Ala Asp Phe Leu Leu Ile Ile Cys Leu
     65                  70                  75                  80

Pro Phe Val Met Asp Tyr Tyr Val Arg Arg Ser Asp Trp Asn Phe Gly
                     85                  90                  95

Asp Ile Pro Cys Arg Leu Val Leu Phe Met Phe Ala Met Asn Arg Gln
                100                 105                 110
```

Gly Ser Ile Ile Phe Leu Thr Val Val Ala Val Asp Arg Tyr Phe Arg
            115                 120                 125

Val Val His Pro His His Ala Leu Asn Lys Ile Ser Asn Trp Thr Ala
    130                 135                 140

Ala Ile Ile Ser Cys Leu Leu Trp Gly Ile Thr Val Gly Leu Thr Val
145                 150                 155                 160

His Leu Leu Lys Lys Leu Leu Ile Gln Asn Gly Pro Ala Asn Val
                165                 170                 175

Cys Ile Ser Phe Ser Ile Cys His Thr Phe Arg Trp His Glu Ala Met
                180                 185                 190

Phe Leu Leu Glu Phe Leu Leu Pro Leu Gly Ile Ile Leu Phe Cys Ser
            195                 200                 205

Ala Arg Ile Ile Trp Ser Leu Arg Gln Arg Gln Met Asp Arg His Ala
            210                 215                 220

Lys Ile Lys Arg Ala Ile Thr Phe Ile Met Val Val Ala Ile Val Phe
225                 230                 235                 240

Val Ile Cys Phe Leu Pro Ser Val Val Val Arg Ile Arg Ile Phe Trp
                245                 250                 255

Leu Leu His Thr Ser Gly Thr Gln Asn Cys Glu Val Tyr Arg Ser Val
            260                 265                 270

Asp Leu Ala Phe Phe Ile Thr Leu Ser Phe Thr Tyr Met Asn Ser Met
            275                 280                 285

Leu Asp Pro Val Val Tyr Tyr Phe Ser Ser Pro Ser Phe Pro Asn Phe
    290                 295                 300

Phe Ser Thr Leu Ile Asn Arg Cys Leu Gln Arg Lys Met Thr Gly Glu
305                 310                 315                 320

Pro Asp Asn Asn Arg Ser Thr Ser Val Glu Leu Thr Gly Asp Pro Asn
                325                 330                 335

Lys Thr Arg Gly Ala Pro Glu Ala Leu Met Ala Asn Ser Gly Glu Pro
            340                 345                 350

Trp Ser Pro Ser Tyr Leu Gly Pro Thr Ser Asn Asn His Ser Lys Lys
        355                 360                 365

Gly His Cys His Gln Glu Pro Ala Ser Leu Glu Lys Gln Leu Gly Cys
    370                 375                 380

Cys Ile Glu
385

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
agcccatagc agatggcaac                                           20

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 23
tgtactttca actttgcatc ctgg                                      24

```
<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 24
aagccaatga caaaccggat aatccctc                                            28
```

METHOD FOR IDENTIFYING SUBSTANCES WHICH POSITIVELY INFLUENCE INFLAMMATORY CONDITIONS OF CHRONIC INFLAMMATORY AIRWAY DISEASES

RELATED APPLICATION

The benefit of prior provisional application Serial No. 60/233,748, filed Sep. 19, 2000 is hereby claimed.

BACKGROUND OF THE INVENTION

The present invention belongs to the field of modulation of inflammatory processes, in particular of inflammatory airway diseases, in which macrophages play an important role. The inflammatory processes can be modulated according to the invention by influencing the function of receptors on macrophages, which receptors are identified to be involved in the inflammatory process.

Inflammatory processes involve a cascade of reactions. A wide variety of factors are involved in inflammatory processes leaving a single treatment to avoid said factors unsuccessful. This is in particular true for inflammatory processes of the airways, like the chronic inflammatory airway diseases.

Chronic inflammatory airway diseases include Chronic Bronchitis and Chronic Obstructive Pulmonary Disease (COPD). For example, COPD is a complex disease encompassing symptoms of several disorders: chronic bronchitis which is characterized by cough and mucus hypersecretion, small airway disease, including inflammation and peribronchial fibrosis, and emphysema. COPD is characterized by an accelerated and irreversible decline of lung function. The major risk factor for developing COPD is continuous cigarette smoking. Since only about 20% of all smokers are inflicted with COPD, a genetic predisposition is also likely to contribute to the disease.

The initial events in the early onset of COPD are inflammatory, affecting small and large airways. An irritation caused by cigarette smoking attracts macrophages and neutrophils the number of which is increased in the sputum of smokers. Perpetual smoking leads to an ongoing inflammatory response in the lung by releasing mediators from macrophages, neutrophils and epithelial cells that recruit inflammatory cells to sites of the injury. So far there is no therapy available to reverse the course of COPD. Smoking cessation may reduce the decline of lung function. Only a few drugs provide some relief for patients. Longlasting β2-agonists and anticholinergics are applied to achieve a transient bronchodilatation. A variety of antagonists for inflammatory events are under investigation like, $LTB_4$-, IL-8-, TNFα-inhibitors.

Chronic inflammatory airway diseases can be attributed to activated inflammatory immune cells, e.g. macrophages. There is a need for modulating the function of macrophages in order to eliminate a basis for inflammatory processes.

SUMMARY OF THE INVENTION

The present invention relates to substances which modulate receptors involved in inflammatory processes and whose modulated functions positively influence inflammatory diseases.

DESCRIPTION OF THE INVENTION

In the present invention it was found that macrophages involved in an inflammatory process, preferably in a chronic inflammatory airway disease, more preferably in chronic bronchitis or COPD, show a pattern of differentially expressed nucleic acid sequence and protein expression which differs from the pattern of gene expression of macrophages from healthy donors or donors in an irritated status, which latter do contain macrophages in an activated status. Therefore, macrophages show different activation levels under different inflammatory conditions, and it is shown in the present invention that macrophages in a hyperactive status are involved in an inflammatory process, preferably in a chronic inflammatory airway disease, more preferably in chronic bronchitis or COPD. The present invention provides for the inhibition of the hyperactivation or the reduction of the hyperactive status of a macrophage by allowing the identification of substances which modulate receptors involved in the hyperactivation or maintaining the hyperactive status.

The invention is based on the identification of a differentially expressed nucleic acid sequence or protein which is involved in causing the induction and/or maintenance of the hyperactive status of macrophages involved in an inflammatory process, preferably in a chronic inflammatory airway disease, more preferably in chronic bronchitis or COPD. Such differentially expressed nucleic acid sequence or protein is in the following named differentially expressed nucleic acid sequence or protein of the invention respectively. In particular, the present invention teaches a link between phenotypic changes in macrophages due to differentially expressed nucleic acid sequence and protein expression pattern and involvement of macrophages in inflammatory processes and, thus, provides a basis for a variety of applications. For example, the present invention provides a method and a test system for determining the expression level of a macrophage protein or differentially expressed nucleic acid sequence of the invention and thereby provides e.g. for methods for diagnosis or monitoring of inflammatory processes with involvement of hyperactivated macrophages in mammalian, preferably human beings, especially such beings suffering from an inflammatory process, preferably in a chronic inflammatory airway disease, more preferably in chronic bronchitis or COPD. The invention also relates to a method for identifying a substance by means of a differentially expressed nucleic acid sequence or protein of the invention processes, which substance modulates, i.e. acts as an inhibitor or activator on the said differentially expressed nucleic acid sequence or protein of the invention and thereby positively influences chronic inflammatory processes by inhibition of the hyperactivation or reduction of the hyperactive status of macrophages, and thereby allows treatment of mammals, preferably human beings, suffering from a said disease. The invention also relates to a method for selectively modulating such a differentially expressed nucleic acid sequence or protein of the invention in a macrophage comprising administering a substance determined to be a modulator of said protein or differentially expressed nucleic acid sequence. The present invention includes the use of said substances for treating beings in need of a treatment of an inflammatory process, preferably a chronic inflammatory airway disease, more preferably chronic bronchitis or COPD.

For the present invention in a first step differentially expressed nucleic acid sequences and proteins are identified which have a different expression pattern in a hyperactivated macrophage compared to a macrophage which is not hyperactivated. For the sake of conciseness this description deals particularly with investigation of macrophages involved in COPD, however, equivalent results may be observed with samples from patients suffering from other chronic inflammatory airway diseases, e.g. chronic bronchitis. The investigation of the different expression pattern leads to the identification of a series of differentially expressed nucleic acid sequences in macrophages, differentially expressed in dependency on the activation status of a macrophage involved in an inflammatory process, as exemplified in the Examples hereinbelow.

Briefly, such a differentially expressed nucleic acid sequence is identified by comparative expression profiling experiments using a cell or cellular extract from a hyperactivated macrophage, i.e. for example from the site of inflammation in a COPD and from the corresponding site of control being not suffering from said disease, however, suffering from an irritated condition like cigarette smoke exposure.

A differentially expressed nucleic acid sequence or protein of the invention can easily be detected by such a method because amongst the differentially expressed macrophage genes a class of differentially expressed nucleic acid sequences can be identified which encodes a class of macrophage surface receptors which is characterized in that it is expressed at a lower or higher level than the control level in a macrophage which is not hyperactivated. Such a macrophage surface receptor of the invention is hereinafter named ILM receptor. However, the invention does not only concern a naturally occurring ILM receptor, but also includes within the meaning of ILM receptor a receptor which is functionally equivalent to, i.e. which shares the binding capacities and the cellular function with an ILM receptor.

An example for an ILM receptor according to the present invention is a FPRL-1 receptor type receptor including FPRL-1 receptor (SEQ ID NO:2). The term "receptor type receptor" used in context with the present invention, e.g. FPRL-1 receptor type receptor, is a receptor which is "functionally equivalent" to, i.e. which shares the binding capacities and the cellular function with, the respective receptor, e.g. FPRL-1 receptor of SEQ. ID NO:2; the term also encompasses variants, mutants or fragments of a naturally occuring receptor, e.g. FPRL-1 receptor. or naturally occuring receptor type receptor, e.g. FPRL-1 receptor type receptor, which variants, mutants or fragments are functionally equivalent to the receptor, e.g. FPRL-1 receptor.

Further examples for ILM receptors are HM74 receptor type receptor including HM74 receptor (SEQ ID NO:21); AICL receptor type receptor including AICL receptor (SEQ ID NO:6); ILT1 receptor type receptor including ILT1 receptor (SEQ ID NO:12); SHPS-1 receptor type receptor including SHPS-1 receptor (SEQ ID NO:4); KDEL receptor 1 type receptor including KDEL receptor 1 (SEQ ID NO:8); and CSF-1 receptor type receptor including CSF-1 receptor (SEQ ID NO:10). Preferred is the respective receptor shown in the sequence listing or a variant, mutant or fragment thereof having the same function, even more preferred is the respective receptor shown in the sequence listing under SEQ ID NOs:21, 6, 12, 4, 8, 10. In even more preferred embodiments the receptors are encoded by the nucleic acid sequences having the SEQ ID NOs:20, 5, 11, 3, 7 or 9, respectively.

A preferred embodiment of an ILM receptor in context with the present invention is a FPRL-1 receptor type receptor. The term FPRL-1 receptor type receptor accordingly also encompasses variants, mutants or fragments, of naturally occuring FPRL-1 receptor or FPRL-1 receptor type receptors, which variants, mutants or fragments are functionally equivalent to the FPRL-1 receptor. An even more preferred embodiment in context with the description of the embodiments of the present invention is the FPRL-1 receptor of SEQ ID NO:2 or a variant, mutant or fragment thereof having the same function, even more preferred is the FPRL-1 receptor of SEQ ID NO:2. In a most preferred embodiment, the FPRL-1 receptor is encoded by the nucleic acid sequence shown in SEQ ID NO:1.

According to the present invention, the function of an ILM receptor expressed at a lower level than the control level is preferably activated in order to inhibit hyperactivation or reduce a hyperactivated status of a macrophage, whereby the function of an ILM receptor which is expressed at a higher level than the control level is preferably inhibited in order to inhibit hyperactivation or reduce a hyperactivated status of a macrophage. A function of a receptor in context with the present invention is any function of a receptor of the invention which is capable of influencing the inflammatory processes. For example, a receptor of the invention mediates inflammation in that it is activated by a ligand (any substance which has the capacity to bind to said receptor to at least one of its domains exposed on the cell surface) and leads to an intracellular signal involved in inflammatory processes.

In one embodiment the present invention concerns a method for determining a substance to be an activator or inhibitor of an ILM receptor characterized in that the receptor is deregulated preferably overexpressed or downregulated in a macrophage involved in a chronic inflammatory airway disease and which receptor plays a role in mediating inflammation. A method according to the invention comprises the application of a substance of interest to a test system which generates a measurable read-out upon modulation of the ILM receptor or of an ILM receptor function. A test system useful for performing such method of the invention comprises a cell or a cell-free system. For example, in one embodiment according to the invention the system is designed in order to allow the testing of substances acting on the expression level of the differentially expressed nucleic acid sequence, in another embodiment the system allows the testing of substances directly interacting with the receptor or interfering with the binding of the receptor with a natural or an artificial but appropriate ligand. The latter system comprises a receptor of the invention in a way that a substance which should be tested can physically contact said receptor and which direct interaction leads to a measurable read-out indicative for the change of receptor function.

A method according to the invention comprising a cellular system can be, for example, a method in which a MonoMac6 or a THP-1 cell is used wherein said cell is stimulated with phorbol 12-myristate 13-acetate and with a substance selected from a group consisting of LPS and smoke.

The present invention also provides a test system for determining whether a substance is an activator or an inhibitor according to the invention of an ILM receptor function according to the invention, characterized in that the receptor is involved in a chronic inflammatory airway disease and which receptor plays a role in mediating inflammation, comprising at least an ILM receptor or an expression vector capable of expressing an ILM receptor in a cell or a host cell transformed with an expression vector capable of expressing an ILM receptor.

For performing a method for determining whether a substance is an activator or an inhibitor of receptor function of the present invention cells as well as cell-free systems can be used. Test systems for performing the method can be, for example, designed and built up by using elements and methods well known in the art. For example, cell-free systems may include, for example, cellular compartments or vesicles comprising a receptor of the invention. Suitable cellular systems include, for example, a suitable prokaryotic cell or eukaryotic cell, i.e. comprising a respective receptor of the invention. A cell suitable for performing a said method of the invention may be obtained by recombinant techniques, i.e. after transformation or transfection with a vector suitable for expression of the desired receptor of the invention, or may be a cell line or a cell isolated from a natural source expressing the desired receptor of the invention. A test system according to the invention comprising a cellular system can also be, for example, a test system in which a MonoMac6 or a THP-1 cell is used wherein said cell is stimulated with phorbol 12-myristate 13-acetate and with a substance selected from a group consisting of LPS and smoke. A test system according to the invention may include a natural or artificial ligand of the receptor if desirable or necessary for testing whether a substance of interest is an inhibitor or activator of a receptor of the invention. Test systems of the invention may be availbale as kits.

A test method according to the invention comprises measuring a read-out, i.e. a phenotypic change in the test system, for example, if a cellular system is used a phenotypic change of the cell. Such change may be a change in a naturally occurring or artificial response of the cell to receptor activation or inhibition, e.g. as detailed in the Examples hereinbelow.

A test method according to the invention can on the one hand be useful for high throughput testing suitable for determining whether a substance is an inhibitor or activator of the invention, but also e.g. for secondary testing or validation of a hit or lead substance identified in high throughput testing.

The present invention also concerns a substance identified in a method according to the invention to be an inhibitor or activator of a receptor of the invention. A substance of the present invention is any compound which is capable of activating or preferably inhibiting a function of a receptor according the invention. An example of a way to activate or inhibit a function of a receptor is by influencing the expression level of said receptor. Another example of a way to activate or inhibit a function of a receptor is to apply a substance which directly binds the receptor, thereby activating or blocking functional domains of said receptor, which can be done reversibly or irreversibly, depending on the nature of the substance applied.

Accordingly, a substance useful for activating or inhibiting receptor function includes substances acting on the expression of a differentially expressed nucleic acid sequence, but also acting on the receptor itself. Therefore, according to the invention the meaning of the term a "substance of the invention" includes but is not limited to nucleic acid sequences coding for the gene of a receptor of the invention or a fragment or variant thereof and being capable of influencing the gene expression level, e.g. nucleic acid molecules suitable as antisense nucleic acid, ribozyme, or for triple helix formation. Another substance of the invention is e.g. an antibody or an organic or inorganic compound directly binding to or interfering with the binding of an appropriate ligand with a receptor of the invention and thereby affecting its function.

In a further aspect, the present invention relates to a method for determining an expression level of an ILM receptor differentially expressed nucleic acid sequence or protein according to the invention comprising determining the level of said ILM receptor in a macrophage according to the invention. Such a method can be used, for example, for testing whether a substance is capable of influencing differentially expressed nucleic acid sequence expression levels in a method outlined above for determining whether a substance is an activator or inhibitor. A method for determining an expression level of an ILM receptor differentially expressed nucleic acid sequence or protein can, however, also be used for testing the activation status of a macrophage, e.g. for diagnostic purposes or for investigation of the success of treatment of a disease which is caused by the hyperactivated macrophage.

Accordingly, the invention also relates to a method for diagnosis of a chronic inflammatory disease or monitoring of such disease, e.g. monitoring success in treating beings in need of treatment of such disease, comprising determining the level of the receptor expressed in a macrophage according to the invention. Said macrophage is preferably a mammalian, more preferably a human cell. Accordingly, macrophages of the present invention are preferably obtainable from the site of inflammation in a mammal and more preferably from a site of inflammation in a human being.

A method for determining expression levels of a receptor according to the invention can, depending on the purpose of determining the expression level, be performed by known procedures such as measuring the concentration of respective RNA transcripts via hybridization techniques or via reporter gene driven assays such as luciferase assays or by measuring the protein concentration of said receptor using respective antibodies to verify the identity of said protein.

The present invention relates to the use of a substance according to the invention for the treatment of a chronic inflammatory airways disease according to the invention. Another embodiment of the present invention relates to a pharmaceutical composition comprising at least one of the substances according to the invention determined to be an activator or an inhibitor using the method for determining whether the substance is an activator or an inhibitor according to the invention characterized in that the respective receptor according to the invention is overexpressed in a macrophage according to the invention involved in a chronic inflammatory airway disease according to the invention. The composition may be manufactured in a manner that is itself known, e.g. by means of conventional mixing, dissolving, granulating, dragee-making, levigating, powdering, emulsifying, encapsulating, entrapping or lyophilizing processes.

In order to use substances activating or inhibiting according to the invention as drugs for treatment of chronic inflammatory airway diseases, the substances can be tested in animal models for example an animal suffering from an inflammatory airway disorder or a transgenic animal expressing a receptor according to the invention.

Toxicity and therapeutic efficacy of a substance according to the invention can be determined by standard pharmaceutical procedures, which include conducting cell culture and animal experiments to determine the $IC_{50}$, $LD_{50}$ and $ED_{50}$. The data obtained are used for determining the animal or more preferred the human dose range, which will also depend on the dosage form (tablets, capsules, aerosol sprays ampules, etc.) and the administration route (for example transdermal, oral, buccal, nasal, enteral, parenteral, inhalative, intratracheal, or rectal).

A pharmaceutical composition containing a least one substance according to the invention as an active ingredient can be formulated in conventional manner. Methods for making such formulations can be found in manuals, e.g. "Remington Pharmaceutical Science". Examples for ingredients that are useful for formulating at least one substance according to the present invention are also found in WO 99/18193, which is hereby incorporated by reference.

In a further aspect the invention teaches a method for treating a chronic inflammatory airway disease according to the invention which method comprises administering to a being preferably to a human being in need of such treatment a suitable amount of a pharmaceutical composition comprising at least one substance determined to be an activator or inhibitor according to a method for determining whether a substance is an activator or an inhibitor according to the invention of an ILM receptor according to the invention characterized in that the receptor is overexpressed in a macrophage according to the invention and plays a role in mediating inflammation involved in a chronic inflammatory airway disease according to the invention.

In another embodiment the invention relates to a method for selectively modulating ILM receptor concentration in a macrophage, comprising administering a substance determined to be an activator or inhibitor of a receptor according to the invention.

Included herein are exemplified embodiments, which are intended as illustrations of single aspects of the invention. Indeed, various modifications of the invention in addition to those herein will become apparent to those skilled in the art from the foregoing description and drawings. Such modifications are intended to fall within the scope of the present invention.

All publications and patent applications cited herein are incorporated by reference in their entireties.

EXAMPLES

Example 1

Comparative Expression Profiling and FPLR-1 Cloning

The following is an illustration of how comparative expression profiling can be performed in order to identify receptors according to the present invention.

1.1. Selection of Patients

Three groups of subjects are studied: healthy non-smokers, healthy smokers and patients with COPD.

In order to assess lung function subjects have to perform spirometry. A simple calculation based on age and height is used to characterise the results. COPD subjects are included if their $FEV_1\%$ predicted is less than 70%. Healthy smokers are age and smoking history matched with the COPD subjects but have normal lung function. Healthy non-smokers have normal lung function and have never smoked. The latter group has a methacholine challenge to exclude asthma. This technique requires increasing doses of methacholine to be given to the subject, with spirometry between each dose. When the $FEV_1$ falls 20% the test is stopped and the $PC_{20}$ is calculated. This is the dose of methacholine causing a 20% fall in $FEV_1$ and we will require a value of greater than 32 as evidence of absence of asthma. All subjects have skin prick tests to common allergens and are required to have negative results. This excludes atopic individuals. The clinical history of the subjects is monitored and examined in order to exclude concomitant disease.

1.2. BAL (Bronchoalveolar Lavage) Procedure

Subjects are sedated with midazolam prior to the BAL. Local anaesthetic spray is used to anaesthetize the back of the throat. A 7 mm Olympus bronchoscope is used. The lavaged area is the right middle lobe. 250 ml of sterile saline is instilled and immediately aspirated. The resulting aspirate contains macrophages.

1.3. BAL Processing

BAL is filtered through sterile gauze to remove debris. The cells are washed twice in HBSS, resuspended in 1 ml HBSS (Hank's Balanced Salt Solution) and counted. The macrophages are spun to a pellet using 15 ml Falcon blue-cap polypropylene, resuspended in Trizol reagent (Gibco BRL Life Technologies) at a concentration of 1 ml Trizol reagent per 10 million cells and then frozen at −70° C.

1.4. Differential Gene Expression Analysis

Total RNA is extracted from macrophage samples obtained according to Example 1.3. Cell suspensions in Trizol are homogenized through pipetting and incubated at room temperature for 5 minutes. 200μ chloroform per ml Trizol is added, the mixture carefully mixed for 15 seconds and incubated for 3 more minutes at room temperature. The samples are spun at 10,000 g for 15 minutes at 4° C. The upper phase is transferred into a new reaction tube and the RNA is precipitated by adding 0.5 ml isopropanol per ml Trizol for 10 minutes at room temperature. Then, the precipitate is pelleted by using a microcentifuge for 10 minutes at 4° C. with 10,000 g, the pellet is washed twice with 75% ethanol, air dried and resuspended in DEPC-$H_2O$.

An RNA cleanup with Qiagen RNeasy Total RNA isolation kit (Qiagen) is performed in order to improve the purity of the RNA. The purity of the RNA is determined by agarose gelelectrophoresis and the concentration is measured by UV absorption at 260 nm. 5 μg of each RNA is used for cDNA synthesis. First and second strand synthesis are performed with the SuperScript Choice system (Gibco BRL Life Technologies). In a total volume of 11 μl RNA and 1 μl of 100 M T7-$(dt)_{24}$ primer, sequence shown in SEQ ID NO:13, are heated up to 70° C. for 10 minutes and then cooled down on ice for 2 minutes. First strand buffer to a final concentration of 1×, DTT to a concentration of 10 mM and a dNTP mix to a final concentration of 0.5 mM are added to a total volume of 18 μl. The reaction mix is incubated at 42° C. for 2 minutes and 2 μl of Superscript II reverse transcriptase (200 U/μl) are added. For second strand synthesis 130 μl of a mix containing 1.15× second strand buffer, 230 μM dNTPs, 10 U E. coli DNA ligase (10 U/μl), E. coli DNA polymerase (10 U/μl), RNase H (2 U/l) is added to the reaction of the first strand synthesis and carefully mixed with a pipette. Second strand synthesis is performed at 16° C. for 2 hours, then 2 μl of T4 DNA polymerase (5 U/μl) are added, incubated for 5 minutes at 16° C. and the reaction is stopped by adding 10 μl 0.5 M EDTA.

Prior to cRNA synthesis the double stranded cDNA is purified. The cDNA is mixed with an equal volume of phenol:chloroform:isoamylalcohol (25:24:1) and spun through the gel matrix of phase lock gels (Eppendorf) in a microcentrifuge in order to separate the cDNA from unbound nucleotides. The aqueous phase is precipitated with ammoniumacetate and ethanol. Subsequently, the cDNA is used for in vitro transcription. cRNA synthesis is performed with the ENZO BioArray High Yield RNA Transcript Labeling Kit according to manufacturer's protocol (ENZO Diagnostics). Briefly, the cDNA is incubated with 1× HY reaction buffer, 1× biotin labeled ribonucleotides, 1× DTT, 1× RNase Inhibitor Mix and 1× T7 RNA Polymerase in a total volume of 40 μl for 5 hours at 37° C. Then, the reaction mix is purified via RNeasy columns (Qiagen), the cRNA precipitated with ammonium acetate and ethanol and finally resuspended in DEPC-treated water. The concentration is determined via UV spectrometry at 260 nm. The remaining cRNA is incubated with 1× fragmentation buffer (5× fragmentation buffer: 200 mM Tris acetate, pH 8.1, 500 mM KOAc, 150 mM MgOAc) at 94° C. for 35 minutes.

For hybridization of the DNA chip 15 µg of cRNA is used, mixed with 50 pM biotin-labeled control B2 oligonucleotide, sequence shown SEQ ID NO:14, 1× cRNA cocktail, 0.1 mg/ml herring sperm DNA, 0.5 mg/ml acetylated BSA, 1× MES (2-[N-morpholino]-ethanesulfonic acid) hybridization buffer in a total volume of 300 µl. The hybridization mixture is heated up to 99° C. for 5 minutes, cooled down to 45° C. for 10 minutes and 200 µl of the mix are used to fill the probe array. The hybridization is performed at 45° C. at 60 rpm for 16 hours. After the hybridization the hybridization mix on the chip is replaced by 300 µl non-stringent wash buffer (100 mM MES, 100 mM NaCl, 0.01% Tween 20). The chip is inserted into an Affymetrix Fluidics station and washing and staining is performed according to the EukGE-WS2 protocol. The staining solution per chip consists of 600 µl 1× stain buffer (100 mM MES, 1 M NaCl, 0.05% Tween 20), 2 mg/ml BSA, 10 µg/ml SAPE (streptavidin phycoerythrin) (Dianova), the antibody solution consists of 1× stain buffer, 2 mg/ml BSA, 0.1 mg/ml goat IgG, 3 µg/ml biotinylated antibody.

After the washing and staining procedure the chips are scanned on the HP Gene Array Scanner (Hewlett Packard).

Data Analysis is performed by pairwise comparisons between chips hybridized with RNA isolated from COPD smokers and chips hybridized with RNA isolated from healthy smokers. One of the different expressed nucleic acid sequences identified is coding for FPRL-1 (formyl peptide receptor like-1) receptor (also named $LXA_4R$, HM63, FPR2, FPRH2, FMLP-R-II, Lipoxin A4 receptor); see SEQ ID NOs:1 and 2. It belongs to the chemoattractant peptide receptor family including receptors for fMLP (N-formyl-methionyl-leucyl-phenylalanine), IL-8 or C5a. These receptors show a seven-transmembrane helix motif and signal through heterotrimeric G-proteins. FPRL-1 receptor was identified as the high-affinity receptor for lipoxin $A_4$ ($LXA_4$) (Murphy, P. M. et al. 1992, J. Biol. Chem. 267:7637–7643).

Alveolar macrophages have been shown to produce lipoxins, which are synthesized by 15-lipoxygenase (Kim, S. J., 1988, Biochem. Biophys Res. Commun. 150:870–876). Lipoxin $A_4$ ($LXA_4$) stimulates chemotaxis, adherence and calcium release in monocytes. In neutrophils, though, $LXA_4$ inhibits chemotaxis and adhesion, and downregulates transmigration through epithelial cells (Maddox, J. F. and Serhan, C. N. 1996, J. Exp. Med. 183:137–146). $LXA_4$ was found elevated in BALs from patients with asthma (Lee, T. H. et al. 1990, Am. Rev. Respir. Dis. 141:1453–1458 and Serhan, J. N. 1999, Lipoxygenases and Their Metabolites, ed. Nigam and Pace-Asciak, Plenum Press, New York 133–149). In particular, it was found to cause a dose-dependent contraction of human bronchi (Christie et al. 1992, Am. Rev. Respir. Dis. 145:1281–1284). $LXA_4$ is considered to be a generic modulator of inflammation in the lung.

1.5. FPRL-1 Receptor Overexpressed in COPD Macrophages

FPRL-1 receptor is consistently found upregulated (66.7%) in COPD smokers compared to healthy smokers. This is demonstrated by calculated "fold change" values from 42 pairwise comparisons and by average difference ("avg diff") values (Table 1, 2). Relative expression levels for non-smokers and healthy smokers are similar and elevated levels are restricted to patients with COPD. Therefore, COPD-specific effects cause the upregulation.

TABLE 1

Expression pattern for FPRL-1 receptor: fold change calculation for 42 pairwise comparisons between COPD and healthy smokers. Only values higher than 2fold and lower than -2fold are considered as deregulated. Thus FPRL-1 receptor was 28 times upregulated and 14 times not regulated.

| fold change | comparison | fold change | comparison | fold change | comparsion |
|---|---|---|---|---|---|
| 2.7 | 39 vs 2 | 2.9 | 5 vs 2 | 3.3 | 1 vs 2 |
| 4.6 | 39 vs 37 | 3.6 | 5 vs 37 | 5.5 | 1 vs 37 |
| 2 | 39 vs 43 | 1.4 | 5 vs 43 | 1.4 | 1 vs 43 |
| 3.1 | 39 vs 56 | 3 | 5 vs 56 | 3.9 | 1 vs 56 |
| 4.1 | 39 vs 57 | 3.2 | 5 vs 57 | 5.3 | 1 vs 57 |
| 2.9 | 39 vs 58 | 3 | 5 vs 58 | 3.6 | 1 vs 58 |
| 2.2 | 39 vs 62 | 2.7 | 5 vs 62 | 2.7 | 1 vs 62 |
| 1.3 | 44 vs 2 | 2.7 | 6 vs 2 | 1.4 | 3 vs 2 |
| 2.7 | 44 vs 37 | 4.1 | 6 vs 37 | 2.9 | 3 vs 37 |
| -1.9 | 44 vs 43 | 1.1 | 6 vs 43 | -1.7 | 3 vs 43 |
| 1.5 | 44 vs 56 | 3.2 | 6 vs 56 | 1.7 | 3 vs 56 |
| 2 | 44 vs 57 | 3.5 | 6 vs 57 | 2.3 | 3 vs 57 |
| 1.4 | 44 vs 58 | 2.9 | 6 vs 58 | 1.5 | 3 vs 58 |
| 1.1 | 44 vs 62 | 2.2 | 6 vs 62 | 1.2 | 3 vs 62 |

TABLE 2

Expression levels of FPRL- 1 receptor: "avg diff" values, a relative indicator of the intensity of the hybridisation signal on the chip, for each patient are listed; OS means obstructed smoker, HS healthy smoker, NS non-smoker

| OS | avg diff | HS | avg diff | NS | avg diff |
|---|---|---|---|---|---|
| P 1 | 1276.7 | P 2 | 490.4 | P 48/49 | 248.2 |
| P 3 | 553.6 | P 37 | 52.1 | P 50/52 | 565.7 |
| P 5 | 1710.2 | P 43 | 940 | P 54/61 | 142.4 |
| P 6 | 1046.9 | P 56 | 327.1 | | |
| P 39 | 1025.2 | P 57 | 238.7 | | |
| P 44 | 507.1 | P 58 | 358.2 | | |
| | | P 62 | 469.6 | | |
| mean + std. dev. | 1020.0 ± 452.5 | | 410.9 ± 276.3 | | 318.8 ± 220.3 |
| Median | 1036.1 | | 327.1 | | 248.2 |

P value for comparisons between COPD smokers and healthy smokers: 0.02

Chip data for FPRL-1 receptor are confirmed by TaqMan analysis (Perkin Elmer Applied Biosystems) for three COPD and two healthy smokers. Fold changes obtained by TaqMan very much resemble the data from the gene chips (Table 3).

TABLE 3

Upregulation of FPRL-1 receptor in COPD smokers determined by gene chips and TaqMan.
Fold change determination for FPRL-1 receptor by chip data in six comparisons between COPD smokers and healthy smokers is validated by analysis of the same samples by TaqMan and the relative upregulation is calculated with GAPDH as a housekeeping gene.

| comparison | chip | TaqMan | comparison | chip | TaqMan |
|---|---|---|---|---|---|
| 1 vs 2 | 3.3 | 4.1 | 1 vs 37 | 5.5 | 4.6 |
| 3 vs 2 | 1.4 | 2.2 | 3 vs 37 | 2.9 | 2.5 |
| 39 vs 2 | 2.7 | 6.0 | 39 vs 37 | 4.6 | 6.8 |

Another differentially expressed nucleic acid sequence identified codes for HM74 receptor, see SEQ ID NOs:20 and 21, which belongs to the family of G-protein-coupled receptors. HM74 receptor was cloned from a human monocytic library (Nomura, H. et al. 1993, Internat. Immunol. 5:1239–1249). To date, the ligand has not been identified. HM74 receptor is consistently found upregulated (54.8%) in COPD smokers compared to healthy smokers. This is demonstrated by calculated "fold change" values (Table 5) from 42 pairwise comparisons and by "avg diff" values (Table 6).

TABLE 5

Expression pattern for HM74 receptor: fold change calculation for 42 pairwise comparisons between COPD and healthy smokers. Only values higher than 2fold and lower than -2fold are considered as deregulated. Thus, HM74 receptor was 23 times upregulated and 17 times not regulated

| fold change | comparison | fold change | comparison | fold change | comparison |
|---|---|---|---|---|---|
| 1.2 | 39 vs 2 | 4.5 | 5 vs 2 | -1.2 | 1 vs 2 |
| 4.7 | 39 vs 37 | 13.8 | 5 vs 37 | 2.8 | 1 vs 37 |
| -2.1 | 39 vs 43 | 2.5 | 5 vs 43 | -2.2 | 1 vs 43 |
| 2.9 | 39 vs 56 | 8.6 | 5 vs 56 | 1.8 | 1 vs 56 |
| 2.6 | 39 vs 57 | 8.9 | 5 vs 57 | 1.6 | 1 vs 57 |
| 2.6 | 39 vs 58 | 7.7 | 5 vs 58 | 1.6 | 1 vs 58 |
| 2.4 | 39 vs 62 | 8.5 | 5 vs 62 | 1.5 | 1 vs 62 |
| 2.8 | 44 vs 2 | 1 | 6 vs 2 | -1.1 | 3 vs 2 |
| 8.8 | 44 vs 37 | 3.5 | 6 vs 37 | 3 | 3 vs 37 |
| 1.5 | 44 vs 43 | -1.7 | 6 vs 43 | -2 | 3 vs 43 |
| 5.5 | 44 vs 56 | 2.2 | 6 vs 56 | 1.9 | 3 vs 56 |
| 5.4 | 44 vs 57 | 2 | 6 vs 57 | 1.7 | 3 vs 57 |
| 4.9 | 44 vs 58 | 1.9 | 6 vs 58 | 1.7 | 3 vs 58 |
| 5.2 | 44 vs 62 | 1.9 | 6 vs 62 | 1.7 | 3 vs 62 |

TABLE 6

Expression levels of HM74 receptor: "avg diff" values, a relative indicator of the intensity of the hybridisation signal on the chip, for each patient are listed; OS means obstructed smoker, HS healthy smoker, NS non-smoker

|  | OS | avg diff | HS | avg diff | NS | avg diff |
|---|---|---|---|---|---|---|
|  | P 1 | 3233 | P 2 | 3916.3 | P 48/49 | 1690.7 |
|  | P 3 | 3474.5 | P 37 | 1154.5 | P 50/52 | 4176.4 |
|  | P 5 | 17671 | P 43 | 5770.5 | P 54/61 | 3504.8 |
|  | P 6 | 4094.2 | P 56 | 1860.2 |  |  |
|  | P 39 | 4201.3 | P 57 | 1639.8 |  |  |
|  | P 44 | 11068.5 | P 58 | 2080.2 |  |  |
|  |  |  | P 62 | 1721.6 |  |  |
| mean + |  | 7290.4 ± |  | 2591.9 ± |  | 3124.0 ± |
| std. dev. |  | 5879.0 |  | 1652.5 |  | 1285.9 |
| median |  | 4147.8 |  | 2243.6 |  | 3504.8 |

Chip data for HM74 receptor are confirmed by TaqMan analysis for three COPD and two healthy smokers. Fold changes obtained by TaqMan very much resemble the data from the gene chips (Table 7).

TABLE 7

Upregulation of HM74 receptor in COPD smokers determined by gene chips and TaqMan.
Fold change determination for HM74 receptor by chip data in six comparisons between COPD smokers and healthy smokers is validated by analysis of the same samples by TaqMan and the relative upregulation is calculated with GAPDH as a housekeeping gene.

| comparison | chip | TaqMan | comparison | chip | TaqMan |
|---|---|---|---|---|---|
| 1 vs 2 | 0.8 | 2.3 | 1 vs 37 | 2.8 | 4.5 |
| 3 vs 2 | 0.9 | 0.8 | 3 vs 37 | 3.0 | 1.4 |
| 39 vs 2 | 1.2 | 1.4 | 39 vs 37 | 4.7 | 2.6 |

Another differentially expressed nucleic acid sequence identified codes for AICL receptor (activation-induced C-type lectin), see SEQ ID NOs:5 and 6., which is a type II membrane protein that recognizes and binds N-acetyl-galactosamin or -glucosamin moieties of plasma glycoproteins (Oda, S. et al. 1988, J. Biochem. 104:600–605). It is expressed in lymphoid tissues and in hematopoetic cells as well as in NK and T cells. Its expression is induced during lymphocyte activation and after stimulation with PMA (Hamann, J. et al. 1997, Immunogenetics 45:295–300). Since homologues of AICL receptor are involved in signal transmission in lymphocytes and in lymphocyte proliferation, it is tempting to assume that AICL receptor also participates in these processes (Hamann, J. et al. 1993, Immunol. 150:4920:4927).

AICL receptor is consistently found upregulated (66.7%) in COPD smokers compared to healthy smokers. This is demonstrated by calculated "fold change" values (Table 8) from 42 pairwise comparisons and by "avg diff" values (Table 9). The p value for the comparisons between COPD smokers and healthy smokers was 0.01.

TABLE 8

Expression pattern for AICL receptor: fold change calculation for 42 pairwise comparisons between COPD and healthy smokers. Only values higher than 2fold and lower than -2fold are considered as deregulated. Thus, AICL receptor was 28 times upregulated and 14 times not regulated

| fold change | comparison | fold change | comparison | fold change | comparison |
|---|---|---|---|---|---|
| 1.2  | 39 vs 2  | 1.5  | 5 vs 2  | -1.3 | 1 vs 2  |
| 1.9  | 39 vs 37 | 2.8  | 5 vs 37 | 1.4  | 1 vs 37 |
| -1.4 | 39 vs 43 | 2.4  | 5 vs 43 | 1.3  | 1 vs 43 |
| 3.3  | 39 vs 56 | 5    | 5 vs 56 | 2.7  | 1 vs 56 |
| 6.9  | 39 vs 57 | 10   | 5 vs 57 | 5.3  | 1 vs 57 |
| 3.1  | 39 vs 58 | 4.5  | 5 vs 58 | 2.3  | 1 vs 58 |
| 3.3  | 39 vs 62 | 5.1  | 5 vs 62 | 2.7  | 1 vs 62 |
| 1.4  | 44 vs 2  | -1.4 | 6 vs 2  | -1.5 | 3 vs 2  |
| 2.6  | 44 vs 37 | 1.2  | 6 vs 37 | 1.2  | 3 vs 37 |
| 2.3  | 44 vs 43 | 1.1  | 6 vs 43 | 1.1  | 3 vs 43 |
| 4.2  | 44 vs 56 | 2.3  | 6 vs 56 | 2.3  | 3 vs 56 |
| 9.6  | 44 vs 57 | 4.5  | 6 vs 57 | 4.5  | 3 vs 57 |
| 4.3  | 44 vs 58 | 2    | 6 vs 58 | 2    | 3 vs 58 |
| 4.2  | 44 vs 62 | 2.3  | 6 vs 62 | 2.3  | 3 vs 62 |

TABLE 9

Expression levels of AICL receptor: "avg diff" values, a relative indicator of the intensity of the hybridisation signal on the chip, for each patient are listed; OS means obstructed smoker, HS healthy smoker, NS non-smoker

| OS | avg diff | HS | avg diff | NS | avg diff |
|---|---|---|---|---|---|
| P 1 | 3415.3 | P 2 | 4984.2 | P 48/49 | 748.4 |
| P 3 | 3412.9 | P 37 | 2388.6 | P 50/52 | 1726.5 |
| P 5 | 6585.8 | P 43 | 2722.5 | P 54/61 | 1087.9 |
| P 6 | 3444.7 | P 56 | 1121.1 | | |
| P 39 | 4548.4 | P 57 | 656.1 | | |
| P 44 | 6291.5 | P 58 | 1476.0 | | |
| | | P 62 | 1113.1 | | |
| mean + std. dev. | 4622.4 ± 1474.3 | | 2065.9 ± 1482.0 | | 1187.5 ± 496.6 |
| median | 3996.6 | | 1476.0 | | 1087.9 |

Another differentially expressed nucleic acid sequence identified codes for ILT1 receptor (immunoglobulin-like transcript 1), see SEQ ID NOs:11 and 12. ILT1 receptor belongs to the Ig superfamily receptors that is related to a subset of activating receptors similar to NK cell receptors for MHC class 1 molecules. ILT1 receptor is a 69 kDa glycosylated transmembrane receptor which is mainly expressed in lung and liver and in monocytes, granulocytes, macrophages, and dendritic cells (Samaridis, J. and Colonna, M., 1997, Eur. J. Immunol. 27:660–665). Upon crosslinking with antibodies ILT1 receptor interacts with the γ-chain of the Fc receptor (FcεRIγ(Nakajima et al., 1999 J. Immunol. 162(1):5–8)

ILT1 receptor is found consistently upregulated (59.5%) in COPD smokers compared to healthy smokers. This is demonstrated by "avg diff" values (Table 10). The p value for the comparisons between COPD smokers and healthy smokers was 0.01.

TABLE 10

Expression levels of ILT1 receptor: "avg diff" values for each patient are listed as well as mean and median values for the three groups of subjects; OS means obstructed smoker, HS healthy smoker, NS non-smoker

| OS | avg diff | HS | avg diff | NS | avg diff |
|---|---|---|---|---|---|
| P 1 | 493.5 | P 2 | 412.3 | P 48/49 | 519.7 |
| P 3 | 1186.0 | P 37 | 457.2 | P 50/52 | 645.0 |
| P 5 | 1097.1 | P 43 | 382.6 | P 54/61 | 491.2 |
| P 6 | 1387.6 | P 56 | 180.5 | | |
| P 39 | 513.5 | P 57 | 367.8 | | |
| P 44 | 1374.5 | P 58 | 720.8 | | |
| | | P 62 | 279.1 | | |
| mean + std. dev. | 1008.8 ± 406.8 | | 400.0 ± 168.6 | | 552.0 ± 81.8 |
| median | 1141.6 | | 382.6 | | 519.7 |

Another differentially expressed nucleic acid sequence identified codes for SHPS-1 receptor (SIRP-alpha1, MYD1, MFR), see SEQ ID NOs:3 and 4, which is known to be highly expressed in macrophages (Fujioka, Y. et al. 1996, Mol. Cell. Biol. 16:6887–6899 and Kharitonenkov, A. et al. 1997, Nature 386:181–186; Brooke, G. P. et al. 1998, Eur J. Immunol. 28:1:11). SHPS-1 receptor is a transmembrane glycoprotein belonging to immunoglobulin superfamily. It contains three extracellular Ig-like domains, a cytoplasmic tail with a potential tyrosine phosphorylation site and an immunoreceptor tyrosine-based inhibitory motif (ITIM). Tyrosine phosphorylation of SHPS-1 receptor occurs upon activation of receptor tyrosine kinases and leads to an association with SHP-1 (in macrophages) and SHP-2 (in non-hematopoetic cells) (Veillette, A. et al. 1998, J. Biol. Chem. 273:22719–22728). Moreover, other proteins have been found to associate with the intracytoplasmic domain of SHPS-1 receptor, and it is therefore tempting to assume that SHPS-1 receptor acts as a scaffolding protein.

SHPS-1 receptor is consistently found downregulated (73.8%) in COPD smokers compared to healthy smokers. This is demonstrated by calculated "fold change" values (Table 11) from 42 pairwise comparisons and by "avg diff" values (Table 12). The p value for the comparisons between COPD smokers and healthy smokers is 0.005.

TABLE 11

Expression pattern for SHPS-1 receptor: fold change calculation for 42 pairwise comparisons between COPD and healthy smokers. Only values higher than 2fold and lower than -2fold are considered as deregulated. Thus, SHPS-1 receptor is 29 times downregulated and 13 times not regulated.

| fold change | comparison | fold change | comparison | fold change | comparsion |
|---|---|---|---|---|---|
| -1.3 | 39 vs 2 | -3.4 | 5 vs 2 | 1.3 | 1 vs 2 |
| -2.8 | 39 vs 37 | -6.8 | 5 vs 37 | -1.7 | 1 vs 37 |
| -1.6 | 39 vs 43 | -8.4 | 5 vs 43 | -2.1 | 1 vs 43 |
| -3.0 | 39 vs 56 | -7.1 | 5 vs 56 | -1.8 | 1 vs 56 |
| -5.6 | 39 vs 57 | -13.2 | 5 vs 57 | -3.4 | 1 vs 57 |
| -5.4 | 39 vs 58 | -12.6 | 5 vs 58 | -3.2 | 1 vs 58 |
| -3.1 | 39 vs 62 | -7.5 | 5 vs 62 | -1.9 | 1 vs 62 |
| 1.4 | 44 vs 2 | -2.1 | 6 vs 2 | -1.1 | 3 vs 2 |
| -1.5 | 44 vs 37 | -4.5 | 6 vs 37 | -2.3 | 3 vs 37 |
| -1.8 | 44 vs 43 | -5.6 | 6 vs 43 | -2.9 | 3 vs 43 |
| -1.6 | 44 vs 56 | -4.7 | 6 vs 56 | -2.4 | 3 vs 56 |
| -2.6 | 44 vs 57 | -8.9 | 6 vs 57 | -4.6 | 3 vs 57 |
| -2.5 | 44 vs 58 | -8.5 | 6 vs 58 | -4.4 | 3 vs 58 |
| -1.7 | 44 vs 62 | -4.9 | 6 vs 62 | -2.5 | 3 vs 62 |

TABLE 12

Expression levels of SHPS-1 receptor: "avg diff" values for each patient are listed as well as mean and median values for the three groups of subjects; OS means obstructed smoker, HS healthy smoker, NS non-smoker

| OS | avg diff | HS | avg diff | NS | avg diff |
|---|---|---|---|---|---|
| P 1 | 1837.8 | P 2 | 1442.6 | P 48/49 | 4979.9 |
| P 3 | 1361.1 | P 37 | 3115.0 | P 50/52 | 1120.5 |
| P 5 | 291.1 | P 43 | 3897.3 | P 54/61 | 2090.6 |
| P 6 | 696.3 | P 56 | 3280.8 | | |
| P 39 | 1105.4 | P 57 | 6220.7 | | |
| P 44 | 2466.0 | P 58 | 5928.9 | | |
| | | P 62 | 3431.7 | | |
| mean ± std. dev. | 1293.0 ± 783.9 | | 3902.4 ± 1671.3 | | 2730.3 ± 2007.7 |
| median | 1233.4 | | 3431.7 | | 2090.6 |

Another differentially expressed nucleic acid sequence identified codes for KDEL receptor 1, see SEQ ID NOs:7 and 8, which is a receptor that has important functions in protein folding and assembly in the endoplasmic reticulum. It recognizes soluble proteins with the amino acid sequence K-D-E-L and retrieves these proteins after binding to the endoplasmic reticulum (Townsley, F. M. et al. 1993, EMBO J. 12:2821–2829). KDEL receptor 1 may be involved in the regulation of protein transport in the Golgi complex. Upon binding of a ligand the KDEL receptor dimerizes and interacts with ARF GAP (GTPase-activating protein for the ADP-ribosylation factor) (Aoe, T. et al 1997, EMBO J. 16:7305–7316).

It is consistently found downregulated (71.4%) in COPD smokers compared to healthy smokers. This is shown by "avg diff" values (Table 13). The p value for the comparisons between COPD smokers and healthy smokers is 0.003.

TABLE 13

Expression levels of KDEL receptor 1: "avg diff" values for each patient are listed as well as mean and median values for the three groups of subjects; OS means obstructed smoker, HS healthy smoker, NS non-smoker

| OS | avg diff | HS | avg diff | NS | avg diff |
|---|---|---|---|---|---|
| P 1 | 877.6 | P 2 | 930.6 | P 48/49 | 1532.9 |
| P 3 | 1227.2 | P 37 | 2151.4 | P 50/52 | 786.4 |
| P 5 | 870.6 | P 43 | 1628.6 | P 54/61 | 1571.5 |
| P 6 | 1188.6 | P 56 | 2232.9 | | |
| P 39 | 1404.5 | P 57 | 2295.1 | | |
| P 44 | 798.1 | P 58 | 2364.1 | | |
| | | P 62 | 2092.0 | | |
| mean ± std. dev. | 1061.1 ± 245.3 | | 1956.4 ± 512.1 | | 1296.9 ± 442.6 |
| median | 1033.1 | | 2151.4 | | 1532.9 |

Another differentially expressed nucleic acid sequence identified codes for the macrophage colony-stimulating factor-1 receptor precursor (CSF-1 receptor, c-fms); see SEQ ID NOs:9 and 10. The CSF-1 receptor belongs to the subfamily of receptor tyrosine kinases. Activation of the CSF-1 receptor results in complex formation of multiple proteins, e.g. CSF-1 receptor, Shc, PI3K, Grb2, Cb1, SHP-1, Src. Moreover, ligand binding also triggers rapid tyrosine phosphorylation of a plethora of cytoplasmic proteins like Cb1, STAT3, STAT5a, STAT5b, p85PI3K, SHP-1, Vav and proteins involved in cytoskeletal organization (Yeung, Y.-G. et al. 1998, J. Biol. Chem. 273:17128–17137). CSF-1 receptor regulates survival, proliferation, differentiation and morphology of mononuclear phagocytes (Hampe, A. et al. 1989, Oncogene Res. 4:9–17).

CSF-1 receptor is consistently found downregulated (45.2%) in COPD smokers compared to healthy smokers. This is shown by "avg diff" values (Table 14). The p value for the comparisons between COPD smokers and healthy smokers is 0.002.

TABLE 14

Expression levels of CSF-1 receptor: "avg diff" values for each patient are listed as well as mean and median values for the three groups of subjects; OS means obstructed smoker, HS healthy smoker, NS non-smoker

| OS | avg diff | HS | avg diff | NS | avg diff |
|---|---|---|---|---|---|
| P 1 | 1136.0 | P 2 | 2591.4 | P 48/49 | 2967.7 |
| P 3 | 2262.5 | P 37 | 3070.6 | P 50/52 | 2041.6 |
| P 5 | 829.5 | P 43 | 2799.2 | P 54/61 | 2376.4 |
| P 6 | 1720.3 | P 56 | 3293.1 | | |
| P 39 | 1860.7 | P 57 | 3703.4 | | |
| P 44 | 1334.1 | P 58 | 1904.9 | | |
| | | P 62 | 2144.5 | | |
| mean + std. dev. | 1523.9 ± 522.7 | | 2786.7 ± 633.2 | | 2461.9 ± 468.9 |
| median | 1527.2 | | 2799.2 | | 2376.4 |

1.6. Use of TaqMan Analysis for Validation of DNA-Chip Data and Diagnosis mRNA-expression profiles obtained by DNA-chips are validated by TaqMan analysis with the same RNA preparations. Moreover, the method is also applied to determine mRNA-levels for FPRL-1 receptor in cultured cell lines and in cells isolated from human beings in order to monitor the progress of the disease.

Total RNA isolated from U937-cells that were treated for 3 days with 10 nM retinoic acid is used in order to optimize of reaction conditions for determining the mRNA-levels of FPRL-1 receptor and setting standard curves for FPRL-1 receptor and GAPDH (glyceraldehyde-3-phosphate dehydrogenase) as a housekeeping gene. Quantification of FPRL-1 receptor is done with the following primers: Forward primer (FP) see SEQ ID NO:17, Reverse primer (RP) see SEQ ID NO:18 and TaqMan probe (TP) see SEQ ID NO:19 labeled with reporter dye FAM at the 5' end and quencher dye TAMRA at the 3' end. For determining mRNA-levels for GAPDH a predeveloped kit "TaqMan GAPDH Control Reagents" (P/N 402869) from Perkin Elmer Applied Biosystems is used. The GAPDH probe is labeled with JOE as the reporter dye and TAMRA as the quencher dye. RT-PCR reactions are performed with the "TaqMan EZ RT-PCR Core Reagents" (P/N N808-0236) kit from Perkin Elmer Applied Biosystems. Standard curves for FPRL-1 receptor and GAPDH are performed with increasing concentrations of RNA from U937 cells treated with 1 µM retinoic acid ranging from 0, 5, 10, 25, 50 to 100 ng per assay. Reaction mixes contain 1× TaqMan EZ-buffer, 3 mM Mn(OAc)$_2$, 300 µM dATP, dCTP, dGTP, and 600 µM dUTP, 2.5 U rTth DNA polymerase, 0.25 U AmpErase UNG in a total volume of 25 µl. For analysis of FPRL-1 receptor reaction mixes include 300 nM of FP and RP and 100 nM of TP. The primer concentrations for determining GAPDH levels are 200 nM for each primer and 100 nM for the GAPDH Taqman probe. In order to determine mRNA levels for FPRL-1 receptor and GAPDH in human subjects and cell lines 16 to 50 ng RNA per reaction are used. All samples are run in triplicate. The reactions are performed with "Micro-Amp Optical 96-well reaction plates" sealed with "Micro-Amp Optical Caps" (Perkin Elmer Applied Biosystems) in an ABI PRISM 7700 Sequence Detection System (Perkin Elmer Applied Biosystems). The PCR conditions are 2 minutes at 50° C., 30 minutes at 60° C., 5 minutes at 95° C., followed by 40 cycles of 20 seconds at 94° C. and 1 minute at 59° C. Data analysis is done either by determining the mRNA levels for FPRL-1 receptor and GAPDH according to the standard curves or by directly relating $C_T$ values for FPRL-1 receptor to $C_T$ values for GAPDH. The latter can be done for these genes since the efficiencies for both reactions are around 95%. The same method is used for investigating mRNA levels isolated from COPD patients in order to diagnose the disease or, after treatment of patients with their putative active drugs to monitor the success of the treatment.

The other receptors mentioned in example 1.5 are investigated accordingly by using the respective appropriate primers.

1.7. Cell Systems

Human monocytic/macrophage cell lines HL-60, U937, THP-1, and MonoMac 6 are used as cellular model systems. Cells are grown in RPMI 1640 media containing 10% FCS supplemented with 100 U/ml penicillin, 100 µg/ml streptomycin, 2 mM glutamine, and 1× non-essential amino acids. The media for MonoMac6 cells also includes 5 ml/l OPI media supplement (Sigma). MonoMac6 cells are exclusively cultured in 24-well plates. Cells are maintained in a humidified atmosphere with 5% $CO_2$ at 37° C. and tested regularly for contamination by mycoplasma.

Differentiation is achieved by adding 10 nM PMA (phorbol 12 myristate-13 acetate) to the media.

1.8. Cloning of FPRL-1 Receptor

FPRL-1 receptor is cloned from a total RNA extracted from U937 cells that were treated with 1 µM retinoic acid for three days. 5 µg RNA is reverse transcribed into cDNA with 5 ng oligo(dt)$_{18}$ primer, 1× first strand buffer, 10 mM DTT, 0.5 mM dNTPs and 2 U Superscript II (Gibco BRL Life Technologies) at 42° C. for 50 minutes. Then, the reaction is terminated at 70° C. for 15 minutes and the cDNA concentration is determined by UV-spectrophotometry. For amplification of FPRL-1 receptor 100 ng of the cDNA and 10 pmol of sequence-specific primers for FPRL-1 receptor (forward primer attB1; see SEQ ID NO:15 and reverse primer attB2; see SEQ ID NO:16) are used for PCR. Reaction conditions are: 2 minutes of 94° C., 35 cycles with 30 seconds at 94° C., 30 seconds at 53° C., 90 seconds at 72° C., followed by 7 minutes at 72° C. with Taq DNA-polymerase. The reaction mix is separated on a 2% agarose gel, a band of about 1,000 bp is cut out and purified with the QIAEX II extraction kit (Qiagen). The concentration of the purified band is determined and about 120 ng are incubated with 300 ng of pDONR201, the donor vector of the Gateway system (Gibco BRL Life Technologies), 1× BP clonase reaction buffer, BP clonase enzyme mix in a total volume of 20 µl for 60 minutes at 25° C. Then, reactions are incubated with 2 µl of proteinase K and incubated for 10 minutes at 37° C. The reaction mix is then electroporated into competent DB3.1 cells and plated on Kanamycin-containing plates. Clones are verified by sequencing. A clone, designated pDONR-HM63 carrying the nucleic acid sequence shown in SEQ ID NO:1 is used for further experiments.

The other receptors mentioned in example 1.5 are cloned using analogous methods.

1.9. Transfection of FPRL-1 Receptor

The vector containing FPRL-1 receptor described under 1.8 is used to transfer the cDNA for FPRL-1 receptor to the expression vector pcDNA3.1 (+)/attR that contains the "attR1" and "attR2" recombination sites of the Gateway cloning system (Gibco BRL Life Technologies) where FPRL-1 receptor is expressed under the control of the CMV promoter. 150 ng of the "entry vector" pDONR-HM63 is mixed with 150 ng of the "destination vector" pcDNA3.1 (+)/attR, 4 µl of the LR Clonase enzyme mix, 4 µl LR Clonase reaction buffer, added up with TE (Tris/EDTA) to 20 µl and incubated at 25° C. for 60 minutes. Then, 2 µl of proteinase K solution is added and incubated for 10 minutes at 37° C. 1 µl of the reaction mix is transformed into 50 µl DH5 by a heat-shock of 30 seconds at 42° C. after incubating cells with DNA for 30 minutes on ice. After heat-shock of the cells 450 µl of S.O.C. is added and cells are incubated at 37° C. for 60 minutes. Cells (100 µl) are plated on LB plates containing 100 µg/ml ampicillin and incubated over night.

A colony that contains pcDNA3.1 (+)/attR with FPRL-1 receptor as an insert is designated pcDNA/FPRL1 and used for transfection studies.

Cell clones containing vectors obtained in 1.8 carrying nucleic acid sequences coding for the other receptors described 1.5 are prepared using analogous methods.

Example 2

Cellular Systems and Phenotypic Effects of FPRL-1 Receptor

Analogous methods as described herein in example 2 for FPRL-1 receptor are also performed using the other receptors described in 1.5.

2.1. Cell Systems

Human monocytic/macrophage cell lines HL-60, U937, THP-1, and MonoMac6 are used as cellular model systems. Cells are grown in RPMI 1640 media containing 10% FCS supplemented with 100 U/ml penicillin, 100 µg/ml streptomycin, 2 mM glutamine, and 1× non-essential amino acids. The media for MonoMac6 also includes 5 ml/l OPI media supplement (Sigma). MonoMac6 cells are exclusively cultured in 24-well plates. All cells are maintained in a humidified atmosphere with 5% $CO_2$ at 37° C. and tested regularly for contamination by mycoplasma.

Differentiation is achieved by adding 10 nM PMA (phorbol 12 myristate-13 acetate) to the media.

Phenotypic Effects of FPRL-1 Receptor (2.2.–2.9.)

2.2. Ligand Binding Assay 300 ml cell culture is harvested with EDTA solution, the suspension is used to spin down the cells at 110–220×g, resuspended in 10 mM Tris/HCl, pH 7.4, 2.5 mM $CaCl_2$, 1.2 mM $MgCl_2$, 40 µg/ml bacitracin, 4 µg/ml leupeptin, 4 µg/ml chymostatin, 10 µg/ml pefabloc, 2 µM phosphoamidon and 0.1 mg/ml bovine serum albumin (BSA Fraktion V, BI Bioproducts) and diluted to $2 \times 10^6$ cells/ml.

0.5 ml aliquots are incubated with 0.3 nM $3^H$-lipoxinA4 (specific activity approximately 10 Ci/mmol) or in the presence of increasing concentrations of untritiated lipoxin A4 (3–300 nM) for 30 minutes at 4° C. The incubation is terminated by harvesting the cells by a Cell-Harvester (Skatron) with GF/B filters, washed three times with 3 ml chilled buffer consisting of 50 mM Tris/HCl, 100 mM NaCl, 10 mM $MgCl_2$, pH 7.4 and the filter-pieces transferred in vials. 2 ml scintillation cocktail is added and the radioactivity determined with a scintillation counter (LKB). Non-specific binding is determined in the presence of 100 nM unlabeled lipoxinA4. A series of peptides and low molecular weight compounds, including the peptide ligand MMK-1 (Klein, C. et al. 1998, Nature Biotech. 16:1334–1337), is used in a concentration range of 0.5 to 300 nM under the same reaction conditions in order to displace tritiated lipoxin A4.

The bound radioactivity (on the filter pieces) is estimated with a counter, the values are recorded on-line and fitted to a model. $IC_{50}$ values for any substance to block binding of $3^H$-lipoxin A4 are calculated.

2.3. $Ca^{2+}$-Release Determined by FLIPR-Assay

FLIPR-assay (Fluorometric Imaging Plate Reader) with FPRL-1 receptor is performed with different CHO cell lines that constitutively express the G-protein α-subunit α16 or the chimeric G-proteins Gqi5 or Gqo5 (these are two Gα(q) chimeras harboring the last five residues of Gα(i) or Gα(o)) and FPRL-1 receptor. The cell lines CHO/Galpha16 (CHO/Galpha16), CHO/GalphaGqi5 and CHOGalphaGqo5 (Boehringer Ingelheim) that constitutively express Gα16, Gqi5 or Gqo5 are transfected with the FPRL-1 receptor expression vector. The cell lines are cultured in Ham's F12 media (Bio Whittaker) with 10% FCS (fetal calf serum), 2 mM glutamine, 200 ng/ml hygromycin, 100 U/ml penicillin and 100 µg/ml streptomycin in a humidified atmosphere with 5% $CO_2$ at 37° C. $3–7 \times 10^5$ cells are seeded in a 60 mm petri dish and grown over night. Cells that are grown to a confluency of 50–80% are used for transfection. 6 µl FuGene6 (Roche Biochemicals) is added to 100 µl of culture media without serum and equilibrated for 5 minutes at room temperature. Then, 2 µg of purified pcDNA/FPRL-1 receptor is added to the prediluted FuGene6 solution, gently mixed, and further incubated at room temperature for 15 minutes. The media is aspirated from the cells and 4 ml of fresh media is added to the cells. The FuGene6/DNA solution is added dropwise to the cells and distributed evenly by swirling of the media. After 48 hours the media is aspirated and replaced by Ham's F12 media, 10% FCS, 2 mM glutamine, 200 ng/ml hygromycin, 100 U/ml penicillin, 100 µg/ml streptomycin, and 200 µg/ml G418. During the following five days the media is replaced daily until dead cells and debris is washed out until single colonies of cells are visible. Single colonies are isolated by separation with cloning cylinders and releasing them from the surface by addition of 100 µl of 1× trypsin/EDTA. Cells are transferred from the cloning cylinders to 4 ml of media and plated in 6 well-plates. Single clones are expanded and the expression of FPRL-1 receptor in several clones is tested via ligand binding assay (2.2.). The cell clone denoted CHO/Galpha16/FPRL-1 receptor, CHO/GalphaGqi5/FPRL-1 receptor, or CHOGalphaGqo5/FPRL-1 receptor with the highest expression of FPRL-1 receptor is used for measuring of intracytoplasmic $Ca^{2+}$ via FLIPR (Molecular Devices).

Cells (CHO/Galpha16/FPRL-1 receptor, CHO/GalphaGqi5/FPRL-1 receptor, or CHOGalphaGqo5/FPRL-1 receptor) are seeded in 384-blackwell plates (Corning) with 2500–5,000 cells per well in a volume of 40 µl and grown overnight in a humidified atmosphere with 5% $CO_2$ at 37° C. As a negative control CHO/Galpha16, CHO/GalphaGqi5 or CHOGalphaGqo5 cells are used. Then, 40 µl of a Fluo-4 (Molecular Probes) staining solution is added to each well in order to label the cells with Fluo-4 at a final concentration of 2 µM. The Fluo-4 staining solution is composed of 10.5 ml cell culture media described above, 420 µl Probenicid solution (1.42 g Probenicid (Sigma), 10 ml 1 M NaOH, 10 ml Hanks buffer), 42 µl Fluo-4 stock solution (50 µg Fluo-4, 23 l DMSO, 23 µl Pluronic F-127 (20% in DMSO) (Molecular Probes), and 420 µl 1M HEPES. After 45 minutes incubation in a humidified atmosphere with 5% $CO_2$ at 37° C. wells are washed with a EMBLA-washer (4 wash steps, program 03) using 2,000 ml Hanks buffer containing 20 ml Probenicid solution as a wash solution and leaving 25 µl wash buffer in each well. Then FLIPR is set to 10,000 counts for stained wells and a difference of 1:5 between unstained and stained wells. Then, 25 µl lipoxin A4 and a series of ligands, peptides, and low molecular weight compounds, including the peptide ligand MMK-1 is added to the wells in increasing concentrations (0.5–300 nM) diluted in Hanks' buffer/0.1% BSA. Substances according to the invention are tested in increasing concentrations (0.5–300 nM) to compete with lipoxin A4 (50 nM) in order to determine their antagonistic potential.

Fluorescence is recorded starting with the addition of the ligand every second for 60 seconds and every 5 seconds for a further 60 seconds.

2.4. Production and Release of Cytokines or Matrix Metalloproteases

Cells of monocytic/macrophage cell lines are treated with lipoxin A4 at cell densities between 2.5 and $5\times10^5$ cells/ml. Cells are harvested after 0, 1, 3, 6, 12, 24, 48, and 72 hours, the supernatant frozen for further investigation, cells are washed with PBS, and resuspended in 400 ml of RLT buffer (from Qiagen RNeasy Total RNA Isolation Kit) with 143 mM β-mercaptoethanol, the DNA sheared with a 20 g needle for at least 5 times and stored at 70° C. Total RNAs are isolated with the Qiagen RNeasy Total RNA Isolation Kit (Qiagen) according to the manufacturer's protocol. Purified RNA is used for TaqMan analysis. The expression levels of cytokines TNFα, IL-1β, IL-8, IL-6, and human matrix metalloproteases, MMP-1, MMP-7, MMP-9, MMP-12, are measured using appropriate primer sequences.

2.4.1. Detection of Secreted Cytokines

Proteins in the supernatants of the cultured and stimulated cells are precipitated by adding TCA (tricholoracetic acid) to a final concentration of 10%. Precipitates are washed twice with 80% ethanol and pellets are resuspended in 50 mM Tris/HCl, pH 7.4, 10 mM $MgCl_2$, 1 mM EDTA. Protein concentration is determined via the Bradford method and 50 μg of each sample are loaded on 12% SDS polyacrylamide gels. Gels are blotted onto PVDF-membranes, blocked for 1 hour in 5% BSA in TBST, and incubated for 1 hour with commercially available antibodies against human TNFα (tumor necrosis factor a) IL-1β (interleukin-1β), IL-8 (interleukin 8), and IL-6 (interleukin 6). After washing with TBST blots are incubated with anti-human IgG conjugated to horseradish-peroxidase, washed again and developed with ECL chemiluminescence kit (Amersham). Intensity of the bands are visualised with BioMax X-ray films (Kodak) and quantified by densitometry.

2.4.2. Detection and Activity of Secreted Matrix Metalloproteases

The procedure is identical to the one described in 2.4.1. Antibodies used for Western blotting are against human MMP-1, MMP-7, MMP-9, and MMP-12.

Protease activity is determined with a fluorescent substrate. Supernatants isolated from stimulated and unstimulated cells (described above) are incubated in a total volume of 50 μl with 1 μM of the substrate (Dabcyl-Gaba-Pro-Gln-Gly-Leu-Glu (EDANS)-Ala-Lys-NH2 (Novabiochem)) for 5 minutes at room temperature. Positive controls are performed with 125 ng purified MMP-12 per reaction. Protease activity is determined by fluorometry with an excitation at 320 nm and an emission at 405 nm.

In an alternative assay to determine proteolytic activity and cell migration a chemotaxis chamber is used. In the wells of the upper part of the chamber cells ($10^5$ cells per well) are plated on filters coated with an 8 μm layer of Matrigel (Becton Dickinson). In the lower compartment chemoattractants like lipoxin A4 (100 nM), MCP-1 (monocyte chemotactic protein 1) (10 ng/ml) are added to the media. After five days filters are removed, cells on the undersurface that have traversed the Matrigel are fixed with methanol, stained with the Diff-Quik staining kit (Dade Behring) and counted in three high power fields (400×) by light microscopy.

2.5. Chemotaxis Assay

In order to determine chemotaxis a 48 well chemotaxis (Boyden) chamber (Neuroprobe) is used. Cells are starved for 24 hours in RPMI media without FCS. Chemoattractants, (50 ng/ml IL-8, 10 ng/ml MCP-1, 10 nM lipoxin A4, 10 nM MMK-1 peptide (2.3.)) are diluted in RPMI media without FCS and 30 μl is placed in the wells of the lower compartment. The upper compartment is separated from the lower compartment by a polycarbonate filter (pore size 8 μm). 50 μl cell suspension ($5\times10^4$) are placed in the well of the upper compartment. The chamber is incubated for 5 hours at 37° C. in a humidified atmosphere with 5% $CO_2$. Then the filter is removed, cells on the upper side are scraped off, cells on the downside are fixed for 5 minutes in methanol and stained with the Diff-Quik staining set (Dade Behring). Migrated cells are counted in three high-power fields (400×) by light microscopy.

2.6. Adherence Assay

Cells are harvested, washed in PBS and resuspended ($4\times10^6$/ml) in PBS and 1 μM BCECF ((2-7-bis-(carboxethyl)-5(6)-carboxyfluorescein acetoxymethyl) ester, Calbiochem) and incubated for 20 minutes at 37° C. Cells are washed in PBS and resuspended ($3.3\times10^6$/ml) in PBS containing 0.1% BSA. $3\times10^5$ cells (90 μl) are added to each well of a 96-well flat bottom plate coated with laminin (Becton Dickinson) and allowed to settle for 10 minutes. 10 μl of agonist (100 nM lipoxin A4 plus lipoxin A4 antagonist) are added and plates are incubated for 20 minutes at 37° C. Then, cells are washed with PBS containing 0.1% BSA and adherent cells are solubilized with 100 μl of 0.025 M NaOH and 0.1% SDS. Quantification is performed by fluorescence measurement.

2.7. Phagocytosis

Cell suspensions ($2.5\times10^4$ cells/ml) are seeded in 6-well plates with 5 ml of U937 or THP-1 or in 24-well plates with 2 ml of MonoMac6 and incubated for 1 hour at 37° C. in a humidified atmosphere with 5% $CO_2$ in the presence of agonists (100 nM lipoxin A4, 50 nM MMK-1 peptide (2.3.)) and low molecular weight compounds according to the invention in order to antagonize agonistic effects. 40 μl of a dispersed suspension of heat-inactivated *Saccharomyces boulardii* (20 yeast/cell) are added to each well. Cells are incubated for three more hours, washed twice with PBS and cytocentrifuged. The cytospin preparations are stained with May-Grünwald-Giemsa and phagocytosed particles are counted by light microsopy.

Example 3

Cell Culture Model for Macrophages Isolated from COPD Patients

Analogous methods as described here in Example 3 for FPRL-1 receptor are also performed using receptors described in 1.5.

As a cell culture model for macrophages isolated from COPD patients we select the monocytic cell lines MonoMac6 and THP-1. In order to mimic a hyperactivated status of these cell lines, cells are treated with PMA. Cells are exposed to further stimuli that are to mimic a condition that is similar to the situation in COPD. These stimuli are exposure to smoke or to LPS.

Expression of FPRL-1 after stimulation of MonoMac6 cells with PMA, smoke, and LPS MonoMac6 cells are cultivated in 24-well plates in RPMI 1640 media, supplemented with 10% FCS (low endotoxin), 2 mM glutamine, 1× non-essential amino acids, 200 U/ml penicillin, 200 μg/ml streptomycin, and 5 ml OPI media supplement (Sigma). Cells are grown to a density of 600,000 cells per well (2 ml media) and stimulated with 10 nM PMA (phorbol 12-myristate 13-acetate) (Sigma), or 20 ng/ml LPS (lipopolysaccharides from *Salmonella minnesota* Re595)

(Sigma). For smoke exposure, cells are incubated in media enriched with smoke for 10 minutes at 37° C., 5% $CO_2$ at a density of $1 \times 10^6$ cells/ml. Enrichment of RPMI 1640 media with smoke is performed with the smoke of two cigarettes. The smoke of the cigarettes is pulled into a 50 ml syringe (about 20 volumes of a 50-ml syringe per cigarette) and then perfused into 100 ml of RPMI 1640 media without supplements. Afterwards, the pH of the smoke-enriched media is adjusted to 7.4 and the media is sterilized through a 0.2 μm filter before use. After the exposure with smoke cells are washed at least twice with RPMI 1640 in order to remove residual smoke particles. Then cells are seeded in 24-well plates with 400,000–600,000 cells per well filled with 2 ml of fresh RPMI 1640 media including the supplements mentioned above.

THP-1 cells are grown in 75 $cm^2$ flasks in RPMI 1640 Glutamax supplemented with 10% FCS (low endotoxin), 200 U/ml penicillin, 200 μg/ml streptomycin. Cells are treated with 10 nM PMA for 48 hours at 37° C., 5% $CO_2$ in order to differentiate the cells to a macrophage-like cell type. Then, media is replaced by new PMA-free cultivation media with the addition of 20 ng/ml LPS.

Both cell types are cultivated at 37° C., 5% $CO_2$ in a humidified atmosphere and cells are harvested at various time points in order to monitor time-dependent effects. Cells are spun down and washed with PBS, resuspended in 400 μl of RLT buffer (Qiagen RNeasy Total RNA Isolation Kit) with 143 mM β-mercaptoethanol, the DNA is sheared with a 20 g needle for at least 5 times and stored at −70° C.

Total RNAs are isolated with the Qiagen RNeasy Total RNA Isolation Kit (Qiagen) according to the manufacturer's protocol. Purified RNA is digested with RNase-free DNase (Qiagen) and used for TaqMan analysis.

TaqMan Analysis

Taqman analysis is used to determine mRNA-levels for FPRL-1 in cell lines after treatment with and without various stimuli at different time points. Total RNA isolated from U937 cells that were treated for 3 days with 10 nM retinoic acid is used in order to optimize reaction conditions for determining the mRNA-levels of FPRL-1 and setting standard curves for FPRL-1 and GAPDH (glyceraldehyde-3-phosphate dehydrogenase) as a housekeeping gene. Quantification of FPRL-1 is done with the following primers: Forward primer (rhHM63 668FP, SEQ ID NO:22), Reverse primer (hHM63 525(+)RP, SEQ ID NO:23) and TaqMan probe (rhHM63 629(−)TP, SEQ ID NO:24) labeled with reporter dye FAM at the 5' end and quencher dye TAMRA at the 3' end. The mRNA-levels for GAPDH are determined with a predeveloped kit for GAPDH "TaqMan GAPDH Control Reagents" (P/N 402869) from PE Applied Biosystems. The GAPDH probe is labeled with JOE as the reporter dye and TAMRA as the quencher dye. RT-PCR reactions are performed with the "TaqMan EZ RT-PCR Core Reagents" (P/N N808–0236) kit from Perkin Elmer. Standard curves for FPRL-1 and GAPDH are performed with increasing concentrations of RNA from U937 cells treated with 1 μM retinoic acid ranging from 0, 5, 10, 25, 50 to 100 ng per assay. Reaction mixes contain 1× TaqMan EZ-buffer, 3 mM $Mn(Oac)_2$, 300 μM dATP, dCTP, dGTP, and 600 μM dUTP, 2.5 U rTth DNA polymerase, 0.25 U AmpErase UNG in a total volume of 25 μl. For analysis of FPRL-1 reaction mixes include 300 nM of rhHM63 668(−)FP and hHM63 525(+)RP and 100 nM of rhHM63 629(−)TP. The primer concentrations for determining GAPDH levels are 200 nM for each primer and 100 nM for the Taqman probe. In order to determine mRNA levels for FPRL-1 and GAPDH in human subjects and cell lines, 16 to 50 ng RNA per reaction are used. All samples are run in triplicate. The reactions are performed with "MicroAmp Optical 96-well reaction plates" sealed with "MicroAmp Optical Caps" (PE Applied Biosystems) in an ABI PRISM 7700 Sequence Detection System (PE Applied Biosystems). The PCR conditions are 2 minutes at 50° C., 30 minutes at 60° C., 5 minutes at 95° C., followed by 40 cycles of 20 seconds at 94° C. and 1 minute at 59° C. Data analysis is done either by determining the mRNA levels for FPRL-1 and GAPDH according to the standard curves or by directly relating $C_T$ values for FPRL-1 to $C_T$ values for GAPDH. The latter procedure can be applied for these genes since the efficiencies for both reactions are in good agreement with each other (around 95%).

TABLE 15

Expression of FPRL-1 in MonoMac6 cells after stimulation with 10 nM PMA

| t (h) | ng FPRL-1 mRNA/ ng GAPDH mRNA |
|---|---|
| 0 | 0.00 |
| 1 | 0.00 |
| 3 | 0.00 |
| 12 | 0.00 |
| 24 | 0.00 |
| 48 | 0.43 |
| 72 | 0.01 |

TABLE 16

Expression of FPRL-1 in MonoMac6 cells after differentiation with 10 nM PMA and stimulation with 20 ng/ml LPS

| t (h) | ng FPRL-1 mRNA/ ng GAPDH mRNA |
|---|---|
| 0 | 0.00 |
| 1 | 0.00 |
| 3 | 0.00 |
| 12 | 1.27 |
| 24 | 2.19 |
| 48 | 2.90 |
| 72 | 1.27 |

TABLE 17

Expression of FPRL-1 in MonoMac6 cells after differentiation with 10 nM PMA and stimulation with smoke

| t (h) | Fold induction of FPRL-1 |
|---|---|
| 0 | 1.00 |
| 1 | 0.02 |
| 3 | 0.14 |
| 6 | 4.44 |
| 12 | 9.90 |
| 25 | 9.35 |
| 48 | 8.73 |

TABLE 18

Expression of FPRL-1 in THP-1 cells after differentiation with PMA and stimulation with LPS

| t (h) | Fold induction of FPRL-1 |
|---|---|
| 0 | 1.00 |
| 1 | 0.23 |
| 3 | 1.81 |
| 9 | 15.77 |
| 24 | 0.82 |
| 48 | 1.59 |

In order to examine the effects of ligands for FPRL-1, MonoMac6 cells are seeded at a density of 250,000 cells/ml in 24-well plates (with 2 ml per well), grown for 24 hours at 37° C., 5% $CO_2$ in a humidified atmosphere before stimulation with 200 nM lipoxin A4 (Biomol), W-peptide (1 μM) (synthesized by Metabion, Martinsried), and LPS (Sigma) as a positive control. Cells are harvested at different time points, and total RNA is isolated as described above using the Qiagen RNeasy Total RNA Isolation Kit (Qiagen). The sequence of the W-peptide (Baek et al. 1996, J. Biol. Chem 271, 8170–8175) is W-K-Y-M-V-m.

The RNA is used for Taqman analysis in order to monitor the expression of inflammatory markers like TNFα, IL-8, and MMP-12.

TABLE 19

Expression of TNFα in MonoMac 6 cells after stimulation with lipoxin A4 and W-peptide

| | Fold Induction | |
|---|---|---|
| t (h) | Lipoxin A4 (200 nM) | W-peptide (1 μM) |
| 0 | 1.00 | 1.00 |
| 3 | 2.43 | 1.03 |

TABLE 20

Expression of IL-8 in MonoMac 6 cells after stimulation with lipoxin A4 and W-peptide

| | Fold Induction | |
|---|---|---|
| t (h) | Lipoxin A4 (200 nM) | W-peptide (1 μM) |
| 0 | 1.00 | 1.00 |
| 3 | 1.99 | 1.54 |

TABLE 21

Expression of MMP-12 in MonoMac 6 cells after stimulation with lipoxin A4 and W-peptide

| | Fold Induction | |
|---|---|---|
| t (h) | Lipoxin A4 (200 nM) | W-peptide (1 μM) |
| 0 | 1.00 | 1.00 |
| 3 | 1.42 | 1.51 |

Since an increased invasion of macrophages in peripheral airways of COPD patients can be observed, we tested the chemotactic ability of MonoMac6 cells which serve as a cell culture model for alveolar macrophages. Chemotaxis of MonoMac6 is determined by administering different ligands for FPRL-1.

MonoMac6 cells are treated with PMA for 24–30 hours in order to induce an activation state of the cells. Cells are harvested, washed twice with RPMI 1640 without supplements, and seeded at a density of 500,000 cells/well (24-well plate) in the presence of 10 nM PMA. After 24–30 hours cells are released from the substratum by repeated rinsing with a pipet, spun down, counted and adjusted to a density of $1 \times 10^6$ cells/ml of RPMI 1640 media without supplements but in the presence of 10 nM PMA. Chemotaxis is performed in a 48-well chemotaxis chamber (Neuroprobe Inc.) and polycarbonate membranes with a pore size of 8 μm (Neuroprobe Inc.). The lower wells of the chamber are filled with 28 μl of different concentrations of lipoxin A4, W-peptide, MCP-1 as a positive control, and RPMI 1640 media without supplements (including 10 nM PMA) as a negative control. The lower wells are covered with the polycarbonate membrane and the upper compartments of the chamber are filled with 50 μl of the cell suspension (50,000 cells per well). After 4 hours of migration at 37° C., 5% $CO_2$ the cells on the upper part of the membrane are scraped off and the cells attached at the lower part of the membrane are stained with the Diff Quik Staining Set (Dade Behring) according to the manufacturer's protocol. Stained cells are counted in 6 to 8 high power fields at a magnification of 250× with a light microscope. The migration index represents the fold increase in the number of cells migrated in response to the chemoattractant over control medium.

TABLE 22

Migration of MonoMac6 cells in resonse to lipoxin A4, W-peptide, and MCP-1

| Stimulus | Migration Index |
|---|---|
| MCP-1 (20 ng/ml) | 2.59 |
| Lipoxin A4 (1 μM) | 1.68 |
| Lipoxin A4 (100 nM) | 1.31 |
| Lipoxin A4 (10 nM) | 0.86 |
| W-peptide (1 μM) | 2.46 |
| W-peptide (100 nM) | 1.23 |
| W-peptide (10 nM) | 0.95 |

The above examples as well as a cell of each of the above cell culture models are used for determining whether a substance is an inhibitor or an activator of an ILM-receptor of the invention which is deregulated in a macrophage according to the invention by adding a substance to be tested and subsequent measuring of a respective above described effect.

What is claimed is:

1. A method for determining whether a substance inhibits or reduces an inflammatory process in which a macrophage is in a hyperactivated status due to a differentially expressed macrophage surface receptor, comprising: (a) applying said substance to a test system which generates a measurable read-out upon modulation of said macrophage surface receptor or macrophage surface receptor function, wherein said macrophage surface receptor is a FPRL-1 receptor comprising SEQ ID NO:2; and (b) comparing the level of the read-out of the test system to a control level, wherein a difference in levels indicates the substance is an inhibitor or an activator of said macrophage surface receptor; and wherein the inhibitor of the macrophage surface receptor which is expressed on a higher level in said hyperactived macrophage or the activator of the macrophage surface receptor which is expressed on a lower level in said hyperactived macrophage indicates the substance inhibits or reduces said hyperactivated status of said macrophage.

2. The method according to claim 1 in which the test system is a cellular system.

3. The method according to claim 2 wherein the cellular system comprises a MonoMac6 cell or a THP-1 cell, and wherein said cell is stimulated with phorbol 12-myristate 13-acetate and with a substance selected from the group consisting of LPS and smoke.

4. The method according to claim 1 in which said receptor is the FPRL-1 receptor having the sequence depicted in SEQ ID NO:2.

5. The method according to claim 1 or claim 2 or claim 3 in which said inflammatory process is chronic obstructive pulmonary disease (COPD).

* * * * *